United States Patent
Shrader et al.

(10) Patent No.: US 7,297,762 B2
(45) Date of Patent: Nov. 20, 2007

(54) MODIFIED AVIAN PANCREATIC POLYPEPTIDE MINIATURE BINDING PROTEINS

(75) Inventors: Alanna Schepartz Shrader, Wilton, CT (US); Jason W. K. Chin, San Diego, CA (US); Reena Zutshi, New Haven, CT (US); Stacey E. Rutledge, New Haven, CT (US); Joanne D. Kehleck Martin, Guilderland, NY (US); Neal J. Zondlo, Arlington, MA (US)

(73) Assignee: Yale University, New Haven, CT (US)

( * ) Notice: Subject to any disclaimer, the term of this patent is extended or adjusted under 35 U.S.C. 154(b) by 528 days.

(21) Appl. No.: 09/840,085

(22) Filed: Apr. 24, 2001

(65) Prior Publication Data

US 2003/0166240 A1 Sep. 4, 2003

Related U.S. Application Data

(60) Provisional application No. 60/271,368, filed on Feb. 23, 2001, provisional application No. 60/265,099, filed on Jan. 30, 2001, provisional application No. 60/240,566, filed on Oct. 16, 2000, provisional application No. 60/199,408, filed on Apr. 24, 2000.

(51) Int. Cl.
C07K 14/465 (2006.01)
C07K 7/00 (2006.01)

(52) U.S. Cl. .................. 530/324; 530/326; 530/327

(58) Field of Classification Search ................ 530/350
See application file for complete search history.

(56) References Cited

U.S. PATENT DOCUMENTS

| | | | |
|---|---|---|---|
| 5,223,409 A | 6/1993 | Ladner et al. | |
| 5,403,484 A | 4/1995 | Ladner et al. | |
| 5,427,908 A | 6/1995 | Dower et al. | |
| 5,516,637 A | 5/1996 | Huang et al. | |
| 5,571,698 A | 11/1996 | Ladner et al. | |
| 5,580,717 A | 12/1996 | Dower et al. | |
| 5,656,725 A * | 8/1997 | Chittenden et al. | 530/324 |
| 5,658,727 A | 8/1997 | Barbas et al. | |
| 5,698,426 A | 12/1997 | Huse | |
| 5,733,743 A | 3/1998 | Johnson et al. | |
| 5,750,753 A | 5/1998 | Kimae et al. | |
| 5,780,225 A | 7/1998 | Wigler et al. | |
| 5,821,047 A | 10/1998 | Garrard et al. | |
| 5,837,500 A | 11/1998 | Ladner et al. | |
| 5,969,108 A | 10/1999 | McCafferty et al. | |

OTHER PUBLICATIONS

Genbank Sequence Accession No. P38803, May 30, 2000.*
Genbank Sequence Accession No. P43316, Dec. 15, 1998.*
Agre et al., 1989, Science 246:922-926.
Ames et al., 1995, J. Immunol. Methods 184:177-186.
Andrews et al., 1999, Tetrahedron 55:11711-11743.
Armstrong et al., 1993, J. Mol. Biol. 230:284-291.
Blackwell et al., 1998, Angew. Chem. Int. Ed. 37:3281-3284.
Blundell et al., 1981, Proc. Natl. Acad. Sci. USA 78:4175-4179.
Braisted et al., 1996, Proc. Natl. Acad. Sci., USA 93:5688-5692.
Brinkmann et al., 1995, J. Immunol. Methods 182:41-50.
Burton et al., 1994, Adv. Immunol. 57:191-280.
Cohen et al., 1972, Proc. Natl. Acad. Sci. USA 69:2110-2114.
Cunningham et al., 1997, Curr. Opin. Struct. Biol. 7:457-462.
Ferré-D'Amaré et al., 1993, Nature 363:38-45.
Flanagan et al., 1998, Annu. Rev. Neurosci. 21:309-345.
Fried et al., 1981, Nucl. Acids Res. 9:6505-6525.
Graham et al., 1973, Virology 52:456-467.
Hoogenboom et al., 1991, Nucleic Acids Res. 19:4133-4137.
Jackson et al., 1991, J. Am. Chem. Soc. 113:9391-9392.
Johnson, 1993, Mol. Cell. Biol. 13:6919-6930.
Keller et al., 1995, J. Mol. Biol. 254:657-667.
Kemp et al., 1991, J. Org. Chem. 56:6683-6697.
Kettleborough et al., 1994, Eur. J. Immunol. 24:952-958.
Kouzarides et al., 1998, Nature 336:646-651.
Kussie et al., 1996, Science 274:948-953.
Li et al., 1992, Biochemistry 31:1245-1253.
Li et al., 1995, Science 270:1657-1660.
Ma et al., 1994, Cell 77:451-459.
Marks et al., 1991, J. Mol. Biol. 222:581-597.
McCafferty et al., 1990, Nature 348:552-554.
Morii et al., 1996, J. Am. Chem. Soc. 118:10011-10017.
Nygren et al., 1997, Curr. Opin. Struct. Biol. 7:463-469.
O'Neil et al., 1990, Science 249:774-778.
Park et al., 1996, J. Am. Chem. Soc. 118:4235-4239.
Persic et al., 1997, Gene 187:9-18.
Radhakrishnan et al., 1997, Cell 91:741-752.
Sattler et al., 1997, Science 275:983-986.
Sauder et al., 1996, J. Gen. Virol. 77:991-996.
Schafmeister et al., 2000, J. Am. Chem. Soc. 122:5891-5892.
Scott et al., 1984, Proc. Natl. Acad. Sci 81:4115-4119.
Segal et al., 2000, Curr. Op. Chem. Biol. 4:34-39.
Shimizu et al., 1997 EMBO J. 16:4689-4697.
Southern, 1975, J. Mol. Biol. 98:503-517.
Southern et al., 1982, J. Mol. Appl. Genet. 1:327-341.
Suckow et al., 1993, EMBO J. 12:1193-1200.
Takahashi et al., 1999, Cell 99:59-69.
Takayama et al., 1997, Methods Mol. Biol. 69:171-184.
Tonan et al., 1990, Biochemistry 29:4424-4429.
Vita et al., 1995, Proc. Natl. Acad. Sci. USA 92:6404-6408.
Vita et al., 1998, Biopolymers 47:93-100.
Weiss et al., 1990, Nature 347:575-578.
Wigler et al., 1979, Proc. Natl. Acad. Sci. USA 76:1373-1376.
Zondlo et al., 1999, J. Am. Chem. Soc. 121:6938-6939.
Akamine, P., et al., "Dynamic Features of cAMP-dependent Protein Kinase Revealed by Apoenzyme Crystal Structure," J. Mol. Biol., 327:159-171 (2003).

(Continued)

Primary Examiner—Marianne P. Allen
(74) Attorney, Agent, or Firm—Wolf, Greenfield & Sacks, P.C.

(57) ABSTRACT

The present invention provides a protein scaffold, such as an avian pancreatic polypeptide, that can be modified by substitution of two or more amino acid residues that are exposed on the alpha helix domain of the polypeptide when the polypeptide is in a tertiary form.

10 Claims, 6 Drawing Sheets

OTHER PUBLICATIONS

Bridges, A., "Chemical Inhibitors of Protein Kinases," Chem Rev., 101:2541-72 (2001).
Cheng, H.C., et al., "A Potent Synthetic Peptide Inhibitor of the cAMP-dependent Protein Kinase," J. Biol. Chem., 261(3):989-992 (1986).
Chin, J. W. and Schepartz, A., "Design and Evolution of a Miniature Bcl-2 Binding Protein", Agnew. Chem. Int. Ed., 20:3806-3809 (2001).
Chin, J.W., and Schepartz, A., "Concerted Evolution of Structure and Function in a Miniature Protein," J. Am. Chem. Soc., 123:2929-2930 (2001).
Cohen, P., "The Development and Therapeutic Potential of Protein Kinase Inhibitors," Current Opinion in Chemical Biology, 3:459-465 (1999).
Du, K., et al., "Characterization of a CREB Gain-of-Function Mutant with Constitutive Transcriptional Activity In Vivo," Mol. Cell. Biol., 20:4320-4327 (2000).
Garcia-Echeverria, C., et al., "Discovery of Potent Antagonists of the Interaction between Human Double Minute 2 and Tumor Supressor p53," J. Med. Chem., 43:3205-3208 (2000).
Glass, D., et al., "Protein Kinase Inhibitor-(6-22)-amide Peptide Analogs with Standard and Nonstandard Amino Acid Substitutions for Phenylalanine 10," J. Biol. Chem., 264:14579-14584 (1989).
Glass, D., et al., "Differential and Common Recognition of the Catalytic Sites of the cGMP-dependent and cAMP-dependent Protein Kinases by Inhibitory Peptides Derived from the Heat-stable Inhibitor Protein," J. Biol. Chem., 261:12166-12171 (1986).
Glass, D., et al., "Primary Structural Determinants Essential for Potent Inhibition of cAMP-dependent Protein Kinase by Inhibitory Peptides Corresponding to the Active Portion of the Heat-stable Inhibitor Protein," J. Biol. Chem., 264:8802-8810 (1989).
Glover, I., et al., "Conformational Flexibility in a Small Globular Hormone: X-Ray Analysis of Avian Pancreatic Polypeptide at 0.98-Å Resolution," Biopolymers, 22:293-304 (1983).
Glover, I., et al., "Crystal Structure of the Heterodimeric bZIP Transcription Factor c-Fos-c-Jun Bound to DNA," Nature, 373:257-261 (1995).
Gonalez, G., et al., "Cyclic AMP Stimulates Somatostatin Gene Transcription by Phosphorylation of CREB at Serine 133," Cell, 59:675-680 (1989).
Hashimoto, Y., et al., "Potent and Preferential Inhibition of $Ca^{2+}$/Calmodulin-Dependent Protein Kinase II by K252a and its Derivative, KT5926," Biochem. Biophys. Res. Comm., 181:423-429 (1991).
Johannessen, M., et al., "Synergistic Activiation of CREB-mediated Transcription by Forskolin and Phorbol Ester Requires PKC and Depends on the Glutamine-rich Q2 Transactivation Domain," Cell. Signal., 16:1187-1199 (2004).
Johnson, D., et al., "Dynamics of cAMP-Dependent Protein Kinase," Chem. Rev., 101:2243-2270 (2001).
Kase, H., et al., "K-252 Compounds, Novel and Potent Inhibitors of Protein Kinase C and Cyclic Nucleotide-Dependent Protein Kinases," Biochem. Biophys. Res. Commun., 142:436-440 (1987).
Kase, H., et al., "K-252a, A Potent Inhibitor of Protein Kinase C from Microbial Origin," J. Antibiot., 39:1059-1065 (1986).
Kettleborough, C., et al., "Isolation of Tumor Cell-specific Single-chain Fv from Immunized Mice Using Phage-antibody Libraries and the Re-construction of Whole Antibodies from these Antibody Fragments," Eur. J. Immunol., 24:952-958 (1994).
Knighton, D., et al., "Structure of a Peptide Inhibitor Bound to the Catalytic Subunit of Cyclic Adenosine Monophosphate-Dependent Protein Kinase," Science, 253:414-420 (1991).
Liljas, A., et al., "Crystal Structure of Human Carbonic Anhydrase C," Nat. New Biol., 235:131-137 (1972).
Meador, W., et al., "Target Enzyme Recognition by Calmodulin: 2.4 § Structure of a Calmodulin-Peptide Complex," Science, 257:1251-1255 (1992).
Mestas, S. and Lumb, K., "Electrostatic Contribution of Phosphorylation to the Stability of the CREB-CBP Activator-Coactivator Complex," Nat. Struct. Biol., 6:613-614 (1999).
Miller, W. T., "Double Trouble," Nat. Struct. Biol., 8:16-18 (2001).
Munson, P., et al., "An Exact Correction to the 'Cheng-Prusoff' Correction," J. Recept. Res., 8:533-546 (1988).
Parker, D., et al., "Role of Secondary Structure in Discrimination between Constitutive and Inducible Activators," Mol. Cell Biol., 19:5601-5607 (1999).
Parker, D., et al., "Analysis of an Activator: Coactivator Complex Reveals an Essential Role for Secondary Structure in Transcriptional Activation," Mol. Cell., 2:353-359 (1998).
Prade, L., et al., "Straurosporine-induced Conformational Changes of cAMP-dependent Protein Kinase Catalytic Subunit Explain Inhibitory Potential," Structure, 5:1627-1637 (1997).
Rutledge, S. et al., "Molecular Recognition of Protein Surfaces: High Affinity Ligands for the CBP KIX Domain," J. Am. Chem. Soc., 125:14336-14347 (2003).
Scapin, G., "Structural Biology in Drug Design: Selective Protein Kinase Inhibitors," Drug Discov. Today, 7:601-611 (2002).
Tapley, P., et al., "K252a is a Selective Inhibitor of the Tyrosine Protein Kinase Activity of the *trk* Family of Oncogenes and Neurotrophin Receptors," Oncogene, 7:371-381 (1992).
Weiss, M., et al., "Folding Transition in the DNA-binding Domain of GCN4 on Specific Binding to DNA," Nature, 347:575-578 (1990).
Whitehouse, S., et al., "Studies on the Kinetic Mechanism of the Catalytic Subunit of the cAMP-dependent Protein Kinase," J. Biol. Chem., 258:3693-3701 (1983).
Wu, X., et al., "The p53-mdm-2 Autoregulatory Feedback Loop," J. Genes Dev., 7:1126-1132 (1993).
Zhang, Z., et al., "Selection and Application of Peptide-binding Peptides," Nat. Biotech., 18:71-74 (2000).
Zheng, J., et al., "A Refined Crystal Structure of the Catalytic Subunit of cAMP-Dependent Protein Kinase Complexed with MnATP and a Peptide Inhibitor," Acta Cryst., D49:362-365 (1993).
Zimmermann, J., et al., "Potent and Selective Inhibitors of the ABL-Kinase: Phenylamino-Pyrimidine (PAP) Derivatives," Bioorg. Med. Chem. Lett., 7:187-192 (1997).
Zor, T., et al., "Roles of Phosphorylation and Helix Propensity in the Binding of the KIX Domain of CREB-binding Protein by Constitutive (c-Myb) and Inducible (CREB) Activators," J. Biol. Chem., 277:42241-42248 (2002).
Chin, Jason W., et al., "Design and Evolution of a Miniature Bcl-2 Binding Protein," Agnew. Chem. Int. Ed. 2001, 40, No. 20, 3806-3809.
Chin, Jason W., et al., Methodology for Optimizing Functional Miniature Proteins Based on Avian Pancreatic Polypeptide Using Phage Display, Bioorganic & Medicinal Chemistry Letters 11 (2001) 1501-1505.
Rutledge, Stacey E., et al., "A view to a kill: ligands for Bcl-2 family proteins," Chemical Biology 2002, 6:479-485.
Wu, Herren, et al., "Building zinc fingers by selection: Toward a therapeutic application," Proc. Natl. Acad. Sci., vol. 92, pp. 344-348, Jan. 1995.
Gunnerson, E. et al., "Affinity maturation of a Taq DNA polymerase specific antibody by helix shuffling," *Protein Engineering*, (Oct. 1999), p. 873-878; vol. 12, No. 10, Oxford University Press, Surrey, GB.

* cited by examiner

FIG. 4

| | | | | | | | | | | | | | | | # | Kd (nM) |
|---|---|---|---|---|---|---|---|---|---|---|---|---|---|---|---|---|
| BakLIB (20-36) | F | V | X | R | L | L | X | Y | I | X | D | X | I | N R | | |
| 4100 | F | V | G | R | L | L | R | Y | F | G | D | E | I | N R | 6 | 401 |
| 4101 | F | V | G | R | L | L | A | Y | F | G | D | D | I | N R | 2 | 811 |
| 4099 | F | V | G | R | L | L | A | Y | F | G | D | T | I | N R | 3 | 352 |
| 4102 | F | V | S | R | L | - | R | Y | I | A | D | L | I | N R | 2 | 3700 |
| | F | V | R | R | L | L | G | Y | I | D | D | I | I | N R | 1 | |
| | F | V | L | R | L | L | W | Y | I | P | D | G | I | N R | 1 | |
| | F | V | R | R | L | L | V | Y | I | W | D | D | I | N R | 1 | |

Top labels: RED, BLUE, RED (positions 3-5), BLUE (position 7), BLUE, RED (positions 9-10)

Bottom labels: BLUE, RED (positions 3-4), LIGHT BLUE (middle positions)

FIG. 5

|  | PP-helix | turn | α-helix | $K_d$ (nM) |
|---|---|---|---|---|
|  | 1 | 8 | 17  20 22  26  29 | |
| aPP | G SQ | TY | GDDAPVEDLIRFYDNLQQYLNVV | |
| p53AD | | | ETFSDLWKLLP | 261 |
| LIBRARY #1 | G SQ | TY | GDDAPVEDLIRFXFXLXWYLLXX | |
| | | | ----------------LIRFQFTLCWYLLWT | |
| p3254 | | | ----------------LIRFQFALRWYLLPM | 334 |
| | | | ----------------LIRFQFSLSWYLLWG | |
| p3255 | | | ----------------LIRFQFGLGWYLLAM | 2800 |
| | | | ----------------LIRFQFTLRWYLLVT | |
| p3548 | | | ----------------LIRFQFPLRWYLLWA | 766 |
| | | | ----------------LIRFQFWLNWYLLWY | |
| p3559 | | | ----------------LIRFKFLLQWYLLAL | 99 |
| | | | ----------------LIRFRFPLRWYLLAL | |
| | | | ----------------LIRFRFQLGWYLLWF | |
| | | | ----------------LIRFSFALQWYLLTR | |
| p3527 | | | ----------------LIRFSFALQWYLLGE | 546 |

SEQUENCE LISTING

<160> NUMBER OF SEQ ID NOS: 73

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
      Recognition site of hsCRE24 protein

<400> SEQUENCE: 1
agtggagatg acagctactc gtgc                                         24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      Recognition site of hsCEBP24 protein

<400> SEQUENCE: 2
agtggagatt gcagctactc gtgc                                         24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      Recognition site of CRE24 protein

<400> SEQUENCE: 3
agtggagatg acgtcatctc gtgc                                         24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      Recognition site of CEBP24 protein

<400> SEQUENCE: 4
agtggagatt gcgcaatctc gtgc                                          24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:  Competitor
      site in recognition studies

<400> SEQUENCE: 5
agtggagtaa ggcctatctc gtgc                                          24

<210> SEQ ID NO 6
<211> LENGTH: 36
<212> TYPE: PRT
<213> ORGANISM: Artificial Sequence
<220> FEATURE:
<223> OTHER INFORMATION: Description of Artificial Sequence:  Segment of
      avian pancreatic polypeptide

<400> SEQUENCE: 6

Gly Pro Ser Gln Pro Thr Tyr Pro Gly Asp Asp Ala Pro Val Glu Asp
 1               5                  10                  15

Leu Ile Arg Phe Tyr Asn Asp Leu Gln Gln Tyr Leu Asn Val Val Thr
            20                  25                  30

Arg His Arg Tyr
        35

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence:  Segment of
      GCN4 protein

<400> SEQUENCE: 7

Asp Pro Ala Ala Leu Lys Arg Ala Arg Asn Thr Glu Ala Ala Arg Arg
 1               5                  10                  15

Ser Arg Ala Arg Lys Leu Gln Arg Met Lys Gln
            20                  25

<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence:  Pancreatic
      polypeptide basic region PPBR0

<400> SEQUENCE: 8

Gly Pro Ser Gln Pro Thr Tyr Pro Gly Asp Asp Ala Pro Val Glu Asp
 1               5                  10                  15

Leu Lys Arg Phe Arg Asn Thr Leu Ala Ala Tyr Leu Ser Val Val Arg
            20                  25                  30

```
Lys Leu Gln Arg Met Lys Gln
        35

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence:  Pancreatic
      polypeptide basic region PPBR10

<400> SEQUENCE: 9

Gly Pro Ser Gln Pro Thr Tyr Pro Gly Asp Asp Ala Pro Val Glu Asp
  1               5                  10                  15

Leu Lys Arg Phe Arg Asn Thr Leu Ala Ala Tyr Leu Ser Arg Leu Arg
             20                  25                  30

Lys Ala Ala Arg Ala Ala Ala
        35

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence:  Pancreatic
      polypeptide basic region PPBR11

<400> SEQUENCE: 10

Gly Pro Ser Gln Pro Thr Tyr Pro Gly Asp Asp Ala Pro Val Glu Asp
  1               5                  10                  15

Leu Lys Arg Phe Arg Asn Thr Leu Ala Ala Arg Leu Ser Arg Leu Arg
             20                  25                  30

Lys Ala Ala Arg Ala Ala Ala
        35

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence:  Pancreatic
      polypeptide basic region PPBR2

<400> SEQUENCE: 11

Gly Pro Ser Gln Pro Thr Tyr Pro Gly Asp Asp Ala Pro Val Glu Asp
  1               5                  10                  15

Leu Lys Arg Phe Arg Asn Thr Leu Ala Ala Arg Arg Ser Arg Ala Arg
             20                  25                  30

Lys Leu Gln Arg Met Lys Gln
        35

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence:  Pancreatic
      polypeptide basic region PPBR4

<400> SEQUENCE: 12

Gly Pro Ser Gln Pro Thr Tyr Pro Gly Asp Asp Ala Pro Val Glu Asp
  1               5                  10                  15

Leu Lys Arg Phe Arg Asn Thr Leu Ala Ala Arg Arg Ser Arg Ala Arg
```

```
                    20                  25                  30

Lys Ala Ala Arg Ala Ala Ala
            35

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence:  G27

<400> SEQUENCE: 13

Asp Pro Ala Ala Leu Lys Arg Ala Arg Asn Thr Glu Ala Ala Arg
  1               5                  10                  15

Ser Arg Ala Arg Lys Leu Gln Arg Met Gln Cys
                20                  25

<210> SEQ ID NO 14
<211> LENGTH: 39
<212> TYPE: PRT
<213> ORGANISM: Artificial Sequence
<220> FEATURE:
<223> OTHER INFORMATION: Description of Artificial Sequence:  Pancreatic
      polypeptide basic region PPBR4-delta

<400> SEQUENCE: 14

Gly Pro Ser Gln Pro Thr Tyr Pro Gly Asp Asp Ala Pro Val Glu Asp
  1               5                  10                  15

Leu Lys Arg Phe Arg Asn Thr Leu Ala Ala Arg Arg Ser Arg Leu Arg
                20                  25                  30

Lys Ala Ala Arg Ala Ala Ala
            35

<210> SEQ ID NO 15
<211> LENGTH: 35
<212> TYPE: PRT
<213> ORGANISM: Artificial Sequence
<220> FEATURE:
<223> OTHER INFORMATION: Description of Artificial Sequence:  Variant
      pancreatic polypeptide basic region, Library A
<221> NAME/KEY: VARIANT
<222> LOCATION: (1)..(7)
<223> OTHER INFORMATION: Xaa at positions 1, 4 and 7 = any amino acid.

<400> SEQUENCE: 15

Xaa Pro Ser Xaa Pro Thr Xaa Pro Gly Asp Asp Ala Pro Val Glu Asp
  1               5                  10                  15

Leu Lys Arg Phe Arg Asn Thr Leu Ala Ala Arg Arg Ser Arg Ala Arg
                20                  25                  30

Lys Ala Ala
        35

<210> SEQ ID NO 16
<211> LENGTH: 35
<212> TYPE: PRT
<213> ORGANISM: Artificial Sequence
<220> FEATURE:
<223> OTHER INFORMATION: Description of Artificial Sequence:  Variant
      pancreatic polypeptide basic region, Library B
<221> NAME/KEY: VARIANT
<222> LOCATION: (2)..(7)
<223> OTHER INFORMATION: Xaa at positions 2, 4, 5 and 7 can be any amino
      acid.

<400> SEQUENCE: 16
```

-continued

```
Gly Xaa Ser Xaa Xaa Thr Xaa Pro Gly Asp Asp Ala Pro Val Glu Asp
 1               5                  10                  15

Leu Lys Arg Phe Arg Asn Thr Leu Ala Ala Arg Arg Ser Arg Ala Arg
                20                  25                  30

Lys Ala Ala
        35
```

<210> SEQ ID NO 17
<211> LENGTH: 35
<212> TYPE: PRT
<213> ORGANISM: Artificial Sequence
<220> FEATURE:
<223> OTHER INFORMATION: Description of Artificial Sequence: Variant
    pancreatic polypeptide basic region, Lib. B, clone
    007

<400> SEQUENCE: 17

```
Gly Gly Ser Arg Ala Thr Met Pro Gly Asp Asp Ala Pro Val Glu Asp
 1               5                  10                  15

Leu Lys Arg Phe Arg Asn Thr Leu Ala Ala Arg Arg Ser Arg Ala Arg
                20                  25                  30

Lys Ala Ala
        35
```

<210> SEQ ID NO 18
<211> LENGTH: 35
<212> TYPE: PRT
<213> ORGANISM: Artificial Sequence
<220> FEATURE:
<223> OTHER INFORMATION: Description of Artificial Sequence: Variant
    pancreatic polypeptide basic region, Lib. B, clone
    012

<400> SEQUENCE: 18

```
Gly Val Ser Val Gly Thr Arg Pro Gly Asp Asp Ala Pro Val Glu Asp
 1               5                  10                  15

Leu Lys Arg Phe Arg Asn Thr Leu Ala Ala Arg Arg Ser Arg Ala Arg
                20                  25                  30

Lys Ala Ala
        35
```

<210> SEQ ID NO 19
<211> LENGTH: 35
<212> TYPE: PRT
<213> ORGANISM: Artificial Sequence
<220> FEATURE:
<223> OTHER INFORMATION: Description of Artificial Sequence: Variant
    pancreatic polypeptide basic region, Lib. B, clone
    011

<400> SEQUENCE: 19

```
Gly Thr Ser Thr Gly Thr Arg Pro Gly Asp Asp Ala Pro Val Glu Asp
 1               5                  10                  15

Leu Lys Arg Phe Arg Asn Thr Leu Ala Ala Arg Arg Ser Arg Ala Arg
                20                  25                  30

Lys Ala Ala
        35
```

<210> SEQ ID NO 20
<211> LENGTH: 35
<212> TYPE: PRT
<213> ORGANISM: Artificial Sequence
<220> FEATURE:
<223> OTHER INFORMATION: Description of Artificial Sequence: Variant

```
      pancreatic polypeptide basic region, Lib. B, clone
      013

<400> SEQUENCE: 20

Gly Val Ser Ser Val Thr Trp Pro Gly Asp Asp Ala Pro Val Glu Asp
 1               5                  10                  15

Leu Arg Lys Phe Arg Asn Thr Leu Ala Ala Arg Arg Ser Arg Ala Arg
            20                  25                  30

Lys Ala Ala
        35

<210> SEQ ID NO 21
<211> LENGTH: 35
<212> TYPE: PRT
<213> ORGANISM: Artificial Sequence
<220> FEATURE:
<223> OTHER INFORMATION: Description of Artificial Sequence:  Variant
      pancreatic polypeptide basic region, Lib. B, clone
      009

<400> SEQUENCE: 21

Gly Pro Ser Glu Gly Thr Glu Pro Gly Asp Asp Ala Pro Val Glu Asp
 1               5                  10                  15

Leu Lys Arg Phe Arg Asn Thr Leu Ala Ala Arg Arg Ser Arg Ala Arg
            20                  25                  30

Lys Ala Ala
        35

<210> SEQ ID NO 22
<211> LENGTH: 35
<212> TYPE: PRT
<213> ORGANISM: Artificial Sequence
<220> FEATURE:
<223> OTHER INFORMATION: Description of Artificial Sequence:  Variant
      pancreatic polypeptide basic region, Lib. B, clone
      016

<400> SEQUENCE: 22

Gly Arg Ser His Gln Thr Trp Pro Gly Asp Asp Ala Pro Val Glu Asp
 1               5                  10                  15

Leu Lys Arg Phe Arg Asn Thr Leu Ala Ala Arg Arg Ser Arg Ala Arg
            20                  25                  30

Lys Ala Ala
        35

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence:
      Peptide 4100 isolated from BakLib

<400> SEQUENCE: 23

Phe Val Gly Arg Leu Leu Arg Tyr Phe Gly Asp Glu Ile Asn Arg
 1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence:
      Peptide 4101 isolated from BakLib
```

-continued

```
<400> SEQUENCE: 24

Phe Val Gly Arg Leu Leu Ala Tyr Phe Gly Asp Asp Ile Asn Arg
  1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:
      Peptide 4099 isolated from BakLib

<400> SEQUENCE: 25

Phe Val Gly Arg Leu Leu Ala Tyr Phe Gly Asp Thr Ile Asn Arg
  1               5                  10                  15

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence:
      Peptide 4102 isolated from BakLib

<400> SEQUENCE: 26

Phe Val Ser Arg Leu Arg Tyr Ile Ala Asp Leu Ile Asn Arg
  1               5                  10

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence:  Peptide
      isolated from BakLib

<400> SEQUENCE: 27

Phe Val Arg Arg Leu Leu Gly Tyr Ile Asp Asp Ile Ile Asn Arg
  1               5                  10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence:  Peptide
      isolated from BakLib

<400> SEQUENCE: 28

Phe Val Leu Arg Leu Leu Trp Tyr Ile Pro Asp Gly Ile Asn Arg
  1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence:  Peptide
      isolated from BakLib

<400> SEQUENCE: 29

Phe Val Arg Arg Leu Leu Val Tyr Ile Trp Asp Asp Ile Asn Arg
  1               5                  10                  15

<210> SEQ ID NO 30
<211> LENGTH: 15
<212> TYPE: PRT
```

```
<213> ORGANISM: Artificial Sequence
<220> FEATURE:
<223> OTHER INFORMATION: Description of Artificial Sequence: Consensus
      sequence for peptides isolated from BakLib
<221> NAME/KEY: VARIANT
<222> LOCATION: (3)..(12)
<223> OTHER INFORMATION: Xaa at positions 3, 7, 10 and 12 can be any
      amino acid.

<400> SEQUENCE: 30

Phe Val Xaa Arg Leu Leu Xaa Tyr Ile Xaa Asp Xaa Ile Asn Arg
 1               5                  10                  15

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence:
      p53 miniature protein p53AD

<400> SEQUENCE: 31

Glu Thr Phe Ser Asp Leu Trp Lys Leu Leu Pro
 1               5                  10

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence:
      p53 miniature protein, Library 1 consensus sequence
<221> NAME/KEY: VARIANT
<222> LOCATION: (21)..(31)
<223> OTHER INFORMATION: Xaa at positions 21, 23, 25, 30, 31 = any amino
      acid.

<400> SEQUENCE: 32

Gly Pro Ser Gln Pro Thr Tyr Pro Gly Asp Asp Ala Pro Val Glu Asp
 1               5                  10                  15

Leu Ile Arg Phe Xaa Phe Xaa Leu Xaa Trp Tyr Leu Leu Xaa Xaa
            20                  25                  30

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence:
      p53 miniature protein, Lib. 1, clone p3254

<400> SEQUENCE: 33

Leu Ile Arg Phe Gln Phe Ala Leu Arg Trp Tyr Leu Leu Pro Met
 1               5                  10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence:
      p53 miniature protein, Lib. 1, clone p3255

<400> SEQUENCE: 34

Leu Ile Arg Phe Gln Phe Gly Leu Gly Trp Tyr Leu Leu Ala Met
 1               5                  10                  15

<210> SEQ ID NO 35
```

```
<211> LENGTH: 15
<212> TYPE: PRT
<213> ORGANISM: Artificial Sequence
<220> FEATURE:
<223> OTHER INFORMATION: Description of Artificial Sequence:
      p53 miniature protein, Lib. 1, clone p3548

<400> SEQUENCE: 35

Leu Ile Arg Phe Gln Phe Pro Leu Arg Trp Tyr Leu Leu Trp Ala
 1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence:
      p53 miniature protein, Lib. 1, clone p3559

<400> SEQUENCE: 36

Leu Ile Arg Phe Lys Phe Leu Leu Gln Trp Tyr Leu Leu Ala Leu
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence:
      p53 miniature protein, Lib. 1, clone p3257

<400> SEQUENCE: 37

Leu Ile Arg Phe Ser Phe Ala Leu Gln Trp Tyr Leu Leu Gly Glu
 1               5                  10                  15

<210> SEQ ID NO 38
<211> LENGTH: 31
<212> TYPE: PRT
<213> ORGANISM: Artificial Sequence
<220> FEATURE:
<223> OTHER INFORMATION: Description of Artificial Sequence:  Universal
      library 1 consensus sequence for pancreatic
      peptide basic region
<221> NAME/KEY: VARIANT
<222> LOCATION: (21)..(29)
<223> OTHER INFORMATION: Xaa at positions 21-23, 25, 26, 29 = any amino
      acid.

<400> SEQUENCE: 38

Gly Pro Ser Gln Pro Thr Tyr Pro Gly Asp Asp Ala Pro Val Glu Asp
 1               5                  10                  15

Leu Ile Arg Phe Xaa Xaa Xaa Leu Xaa Xaa Tyr Leu Xaa Val Val
                20                  25                  30

<210> SEQ ID NO 39
<211> LENGTH: 142
<212> TYPE: DNA
<213> ORGANISM: Artificial Sequence
<220> FEATURE:
<223> OTHER INFORMATION: Description of Artificial Sequence:  Cloning
      primer APP.TS

<400> SEQUENCE: 39
ctatgcggcc cagccggccg gtccgtccca gccgacctac ccgggtgacg acgcaccggt      60
tgaagatctg atccgtttct acaacgacct gcagcagtac ctgaacgttg ttacccgtca     120
ccgttacgcg gccgcaggtg cg                                              142
```

```
<210> SEQ ID NO 40
<211> LENGTH: 87
<212> TYPE: DNA
<213> ORGANISM: Artificial Sequence
<220> FEATURE:
<223> OTHER INFORMATION: Description of Artificial Sequence:  Cloning
      primer APP.BS

<400> SEQUENCE: 40
ctatgcggcc cagccggccg gtccgtccca gccgacctac cccgggtgac gacgcaccgg      60
ttgaagatct gatccgtttc tacaacg                                         87

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence:  PCR primer

<400> SEQUENCE: 41
ctatgcggcc cagccggccg g                                               21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:  PCR primer

<400> SEQUENCE: 42
cgcacctgcg gccgcgtaac g                                               21

<210> SEQ ID NO 43
<211> LENGTH: 83
<212> TYPE: DNA
<213> ORGANISM: Artificial Sequence
<220> FEATURE:
<223> OTHER INFORMATION: Description of Artificial Sequence:  Cloning
      primer PPBR4TS

<400> SEQUENCE: 43
gatctgaagc gctttcgtaa caccctggct gcgcgccgtt cccgtgcacg taaagctgca      60
cgtgctgcag ctggtggttg cgc                                             83

<210> SEQ ID NO 44
<211> LENGTH: 103
<212> TYPE: DNA
<213> ORGANISM: Artificial Sequence
<220> FEATURE:
<223> OTHER INFORMATION: Description of Artificial Sequence:  Cloning
      primer PPBR4BS

<400> SEQUENCE: 44
cgcacctgcg gccgcgcaac caccagctgc agcacgtgca gctttacgtg cacgggaacg      60
gcgcgcagcc aggtgttac gaaagcgctt cagatcttca acc                        103

<210> SEQ ID NO 45
<211> LENGTH: 96
<212> TYPE: DNA
<213> ORGANISM: Artificial Sequence
<220> FEATURE:
<223> OTHER INFORMATION: Description of Artificial Sequence:
      Oligonucleotide for constructing library
<221> NAME/KEY: variation
<222> LOCATION: (40)..(69)
```

```
<223> OTHER INFORMATION: n at positions 40, 41, 52, 53, 61, 62, 67, 68 =
      any nucleotide; s at positions 42, 54, 63, 69 = c
      or g.

<400> SEQUENCE: 45
ggtgacgacg caccggttga agatctgatc cgctttgttn nscgtctgct gnnstacatc      60
nnsgacnnsa tcaaccgtcg tgcggccgca ggtgcg                                96

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide for constructing library

<400> SEQUENCE: 46
cgcacctgcg gcggcacgac g                                                21

<210> SEQ ID NO 47
<211> LENGTH: 41
<212> TYPE: PRT
<213> ORGANISM: Artificial Sequence
<220> FEATURE:
<223> OTHER INFORMATION: Description of Artificial Sequence:  PPEBP1,
      polyproline-enhancer binding protein

<400> SEQUENCE: 47

Gly Pro Ser Gln Pro Thr Tyr Pro Gly Asp Asp Ala Pro Val Tyr Asp
 1               5                  10                  15

Leu Ile Arg Phe Arg Asn Asn Leu Ala Val Arg Lys Ser Arg Val Lys
            20                  25                  30

Ala Lys Arg Arg Asn Gln Gly Gly Cys
        35                  40

<210> SEQ ID NO 48
<211> LENGTH: 41
<212> TYPE: PRT
<213> ORGANISM: Artificial Sequence
<220> FEATURE:
<223> OTHER INFORMATION: Description of Artificial Sequence:  PPEBP2,
      polyproline-enhancer binding protein

<400> SEQUENCE: 48

Gly Pro Ser Gln Pro Thr Tyr Pro Gly Asp Asp Ala Pro Glu Tyr Arg
 1               5                  10                  15

Leu Arg Arg Phe Arg Asn Asn Leu Ala Val Arg Lys Ser Arg Val Lys
            20                  25                  30

Ala Lys Arg Arg Asn Gln Gly Gly Cys
        35                  40

<210> SEQ ID NO 49
<211> LENGTH: 41
<212> TYPE: PRT
<213> ORGANISM: Artificial Sequence
<220> FEATURE:
<223> OTHER INFORMATION: Description of Artificial Sequence:  PPEBP3,
      polyproline-enhancer binding protein

<400> SEQUENCE: 49

Gly Pro Ser Gln Pro Thr Tyr Pro Gly Asp Asp Ala Pro Val Tyr Asp
 1               5                  10                  15

Leu Ile Arg Phe Arg Asn Asn Leu Ala Val Tyr Leu Ser Val Val Lys
            20                  25                  30
```

```
Ala Lys Arg Arg Asn Gln Gly Gly Cys
        35                  40

<210> SEQ ID NO 50
<211> LENGTH: 41
<212> TYPE: PRT
<213> ORGANISM: Artificial Sequence
<220> FEATURE:
<223> OTHER INFORMATION: Description of Artificial Sequence:  PPEBP4,
      polyproline-enhancer binding protein

<400> SEQUENCE: 50

Gly Pro Ser Gln Pro Thr Tyr Pro Gly Asp Asp Ala Pro Val Ala Arg
  1               5                  10                  15

Leu Arg Arg Phe Ala Ala Thr Leu Ala Ala Ala Ser Ala Ala Lys
            20                  25                  30

Ala Lys Arg Arg Asn Gln Gly Gly Cys
        35                  40

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence:  EBP1,
      polyproline-enhancer binding protein

<400> SEQUENCE: 51

Val Tyr Asp Leu Ile Arg Phe Arg Asn Asn Leu Ala Val Arg Lys Ser
  1               5                  10                  15

Val Val Lys Ala Lys Arg Arg Asn Gln Gly Gly Cys
            20                  25

<210> SEQ ID NO 52
<211> LENGTH: 41
<212> TYPE: PRT
<213> ORGANISM: Artificial Sequence
<220> FEATURE:
<223> OTHER INFORMATION: Description of Artificial Sequence:
      Delta-PPEBP1, polyproline-enhancer binding protein

<400> SEQUENCE: 52

Gly Pro Ser Trp Pro Thr Tyr Pro Gly Asp Asp Ala Pro Val Tyr Asp
  1               5                  10                  15

Leu Ile Arg Phe Arg Asn Asn Leu Ala Val Arg Lys Ser Val Val Lys
            20                  25                  30

Ala Lys Arg Arg Asn Gln Gly Gly Cys
        35                  40

<210> SEQ ID NO 53
<211> LENGTH: 34
<212> TYPE: PRT
<213> ORGANISM: Artificial Sequence
<220> FEATURE:
<223> OTHER INFORMATION: Description of Artificial Sequence:  PPMyo1,
      Myo D peptide

<400> SEQUENCE: 53

Gly Pro Ser Gln Pro Thr Tyr Pro Gly Asp Asp Ala Pro Val Glu Asp
  1               5                  10                  15

Leu Arg Arg Phe Tyr Asp Thr Leu Arg Glu Arg Arg Arg Val Val Gly
            20                  25                  30
Gly Cys
```

```
<210> SEQ ID NO 54
<211> LENGTH: 34
<212> TYPE: PRT
<213> ORGANISM: Artificial Sequence
<220> FEATURE:
<223> OTHER INFORMATION: Description of Artificial Sequence: PPMyo2,
      MyoD peptide

<400> SEQUENCE: 54

Gly Pro Ser Gln Pro Thr Tyr Pro Gly Asp Asp Ala Pro Val Glu Asp
 1               5                  10                  15

Leu Arg Arg Phe Tyr Asp Thr Leu Arg Glu Tyr Leu Arg Val Val Gly
            20                  25                  30
Gly Cys

<210> SEQ ID NO 55
<211> LENGTH: 34
<212> TYPE: PRT
<213> ORGANISM: Artificial Sequence
<220> FEATURE:
<223> OTHER INFORMATION: Description of Artificial Sequence: PPMyo3,
      MyoD peptide

<400> SEQUENCE: 55

Gly Pro Ser Gln Pro Thr Tyr Pro Gly Asp Asp Ala Pro Val Glu Asp
 1               5                  10                  15

Leu Arg Arg Phe Tyr Asp Thr Leu Arg Glu Tyr Arg Arg Val Val Gly
            20                  25                  30

Gly Cys

<210> SEQ ID NO 56
<211> LENGTH: 34
<212> TYPE: PRT
<213> ORGANISM: Artificial Sequence
<220> FEATURE:
<223> OTHER INFORMATION: Description of Artificial Sequence: PPMyo4,
      MyoD peptide

<400> SEQUENCE: 56

Gly Pro Ser Gln Pro Thr Tyr Pro Gly Asp Asp Ala Pro Val Glu Asp
 1               5                  10                  15

Leu Arg Arg Phe Tyr Asp Thr Leu Arg Glu Arg Leu Arg Val Val Gly
            20                  25                  30

Gly Cys

<210> SEQ ID NO 57
<211> LENGTH: 31
<212> TYPE: PRT
<213> ORGANISM: Artificial Sequence
<220> FEATURE:
<223> OTHER INFORMATION: Description of Artificial Sequence: PPeng1,
      Q50K engrailed variant peptide

<400> SEQUENCE: 57

Gly Pro Ser Gln Pro Thr Tyr Pro Gly Asp Asp Ala Pro Lys Ile Trp
 1               5                  10                  15

Leu Lys Asn Phe Arg Asp Lys Leu Lys Lys Tyr Leu Asn Val Val
            20                  25                  30

<210> SEQ ID NO 58
<211> LENGTH: 31
<212> TYPE: PRT
<213> ORGANISM: Artificial Sequence
<220> FEATURE:
```

```
<223> OTHER INFORMATION: Description of Artificial Sequence: PPeng2,
      Q50K engrailed variant peptide

<400> SEQUENCE: 58

Gly Pro Ser Gln Pro Thr Tyr Pro Gly Asp Asp Ala Pro Lys Ile Trp
 1               5                  10                  15

Leu Lys Asn Phe Arg Ala Lys Leu Lys Lys Tyr Leu Asn Val Val
             20                  25                  30

<210> SEQ ID NO 59
<211> LENGTH: 31
<212> TYPE: PRT
<213> ORGANISM: Artificial Sequence
<220> FEATURE:
<223> OTHER INFORMATION: Description of Artificial Sequence: PPeng3,
      Q50K engrailed variant peptide

<400> SEQUENCE: 59

Gly Pro Ser Gln Pro Thr Tyr Pro Gly Asp Asp Ala Pro Val Glu Asp
 1               5                  10                  15

Leu Lys Ile Phe Tyr Lys Asn Leu Arg Gln Tyr Leu Lys Val Val
             20                  25                  30

<210> SEQ ID NO 60
<211> LENGTH: 31
<212> TYPE: PRT
<213> ORGANISM: Artificial Sequence
<220> FEATURE:
<223> OTHER INFORMATION: Description of Artificial Sequence: PPeng4,
      Q50K engrailed variant peptide

<400> SEQUENCE: 60

Gly Pro Ser Gln Pro Thr Tyr Pro Gly Asp Asp Ala Pro Val Glu Asp
 1               5                  10                  15

Leu Lys Ile Phe Phe Lys Asn Leu Arg Ala Lys Leu Lys Lys Val
             20                  25                  30

<210> SEQ ID NO 61
<211> LENGTH: 43
<212> TYPE: PRT
<213> ORGANISM: Artificial Sequence
<220> FEATURE:
<223> OTHER INFORMATION: Description of Artificial Sequence: PPFos1,
      Fos peptide

<400> SEQUENCE: 61

Gly Pro Ser Gln Pro Thr Tyr Pro Gly Asp Asp Ala Pro Val Leu Glu
 1               5                  10                  15

Leu Glu Asn Phe Tyr Leu Asn Leu Glu Ile Tyr Leu Leu Val Val Glu
             20                  25                  30

Lys Glu Lys Leu Glu Phe Ile Leu Ala Ala Tyr
         35                  40

<210> SEQ ID NO 62
<211> LENGTH: 43
<212> TYPE: PRT
<213> ORGANISM: Artificial Sequence
<220> FEATURE:
<223> OTHER INFORMATION: Description of Artificial Sequence: PPFos2,
      Fos peptide

<400> SEQUENCE: 62

Gly Pro Ser Gln Pro Thr Tyr Pro Gly Asp Asp Ala Pro Val Leu Glu
 1               5                  10                  15
```

Leu Glu Lys Phe Tyr Leu Asn Leu Glu Ile Tyr Leu Val Val Glu
            20                  25                  30

Lys Glu Lys Leu Glu Phe Ile Leu Ala Ala Tyr
            35                  40

<210> SEQ ID NO 63
<211> LENGTH: 50
<212> TYPE: PRT
<213> ORGANISM: Artificial Sequence
<220> FEATURE:
<223> OTHER INFORMATION: Description of Artificial Sequence:  PPFos3,
      Fos peptide

<400> SEQUENCE: 63

Gly Pro Ser Gln Pro Thr Tyr Pro Gly Asp Asp Ala Pro Val Leu Asp
 1               5                  10                  15

Leu Glu Thr Phe Tyr Leu Glu Leu Glu Asn Tyr Leu Leu Val Val Glu
            20                  25                  30

Ile Ala Asn Leu Leu Lys Glu Lys Glu Lys Leu Glu Phe Ile Leu Ala
            35                  40                  45

Ala Tyr
    50

<210> SEQ ID NO 64
<211> LENGTH: 50
<212> TYPE: PRT
<213> ORGANISM: Artificial Sequence
<220> FEATURE:
<223> OTHER INFORMATION: Description of Artificial Sequence:  PPFos4,
      Fos peptide

<400> SEQUENCE: 64

Gly Pro Ser Gln Pro Thr Tyr Pro Gly Asp Asp Ala Pro Val Leu Asp
 1               5                  10                  15

Leu Glu Thr Phe Tyr Leu Glu Leu Glu Lys Tyr Leu Leu Val Val Glu
            20                  25                  30

Ile Ala Asn Leu Leu Lys Glu Lys Glu Lys Leu Glu Phe Ile Leu Ala
            35                  40                  45

Ala Tyr
    50

<210> SEQ ID NO 65
<211> LENGTH: 5
<212> TYPE: DNA
<213> ORGANISM: Artificial Sequence
<220> FEATURE:
<223> OTHER INFORMATION: Description of Artificial Sequence:  CRE
      half-site promoter

<400> SEQUENCE: 65 atgac                                                                    5

<210> SEQ ID NO 66
<211> LENGTH: 5
<212> TYPE: DNA
<213> ORGANISM: Artificial Sequence
<220> FEATURE:
<223> OTHER INFORMATION: Description of Artificial Sequence:  C/EBP
      half-site promoter

<400> SEQUENCE: 66 attgc                                                                    5

```
<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence:  C/EBP
      protein binding site

<400> SEQUENCE: 67
attgcgcaat                                                          10

<210> SEQ ID NO 68
<211> LENGTH: 10
<212> TYPE: DNA
<213> ORGANISM: Artificial Sequence
<220> FEATURE:
<223> OTHER INFORMATION: Description of Artificial Sequence:  CRE
      protein binding site

<400> SEQUENCE: 68
atgacgtcat                                                          10

<210> SEQ ID NO 69
<211> LENGTH: 31
<212> TYPE: PRT
<213> ORGANISM: Artificial Sequence
<220> FEATURE:
<223> OTHER INFORMATION: Description of Artificial Sequence:
      Transcription-activating miniature protein,
      consensus sequence
<221> NAME/KEY: VARIANT
<222> LOCATION: (2)..(8)
<223> OTHER INFORMATION: Xaa at positions 2, 4, 5, 7, 8 = any amino
      acid.

<400> SEQUENCE: 69

Gly Xaa Ser Xaa Xaa Thr Xaa Xaa Gly Asp Asp Ala Pro Val Arg Arg
  1               5                  10                  15

Leu Ser Phe Phe Tyr Ile Leu Leu Asp Leu Tyr Leu Asp Ala Pro
             20                  25                  30

<210> SEQ ID NO 70
<211> LENGTH: 31
<212> TYPE: PRT
<213> ORGANISM: Artificial Sequence
<220> FEATURE:
<223> OTHER INFORMATION: Description of Artificial Sequence:  PPKID1,
      transcription-activating miniature protein

<400> SEQUENCE: 70

Gly Ala Ser Asp Met Thr Tyr Trp Gly Asp Asp Ala Pro Val Arg Arg
  1               5                  10                  15

Leu Ser Phe Phe Tyr Ile Leu Leu Asp Leu Tyr Leu Asp Ala Pro
             20                  25                  30

<210> SEQ ID NO 71
<211> LENGTH: 31
<212> TYPE: PRT
<213> ORGANISM: Artificial Sequence
<220> FEATURE:
<223> OTHER INFORMATION: Description of Artificial Sequence:  PPKID2,
      transcription-activating miniature protein

<400> SEQUENCE: 71

Gly Met Ser Arg Val Thr Pro Gly Gly Asp Asp Ala Pro Val Arg Arg
  1               5                  10                  15

Leu Ser Phe Phe Tyr Ile Leu Arg Asp Leu Tyr Leu Asp Ala Pro
```

-continued

```
                    20                  25                  30

<210> SEQ ID NO 72
<211> LENGTH: 31
<212> TYPE: PRT
<213> ORGANISM: Artificial Sequence
<220> FEATURE:
<223> OTHER INFORMATION: Description of Artificial Sequence:  PPKID3,
      transcription-activating miniature protein

<400> SEQUENCE: 72

Gly Ala Ser Pro His Thr Ser Ser Gly Asp Asp Ala Pro Val Arg Arg
 1               5                  10                  15

Leu Ser Phe Phe Asp Ile Leu Leu Asp Leu Tyr Leu Asp Ala Pro
                20                  25                  30

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence:  BH3
      domain of Bak peptide

<400> SEQUENCE: 73

Gly Gln Val Gly Arg Gln Leu Ala Ile Ile Gly Asp Asp Ile Asn Arg
 1               5                  10                  15
```

…

MODIFIED AVIAN PANCREATIC POLYPEPTIDE MINIATURE BINDING PROTEINS

CROSS REFERENCE TO RELATED APPLICATIONS

This application claims the benefit of U.S. Provisional Applications No. 60/199,408 filed Apr. 24, 2000; No. 60/240,566 filed Oct. 16, 2000; and U.S. Provisional Applications entitled "Small Polypeptide Molecules that Bind DNA or Proteins with High Affinity and Specificity": No. 60/265,099 filed Jan. 30, 2001 and No. 60/271,368 filed Feb. 23, 2001. These applications are incorporated herein by reference in their entirety.

STATEMENT OF GOVERNMENT SUPPORT

This invention was partially made with government support under National Institute of Health Grants 5-R01-GM59483 and 1-R01-GM65453-01.

FIELD OF THE INVENTION

The present invention relates to a polypeptide scaffold, such as an avian pancreatic polypeptide, that is modified by substitution of at least one amino acid residue that is exposed on the alpha helix domain of the polypeptide when the polypeptide is in a tertiary form. The invention also relates to phage display libraries for such scaffolds.

BACKGROUND OF THE INVENTION

Many proteins recognize nucleic acids, other proteins or macromolecular assemblies using a partially exposed alpha helix. Within the context of a native protein fold, such alpha helices are usually stabilized by extensive tertiary interactions with residues that may be distant in primary sequence from both the alpha helix and from each other. With notable exceptions (Armstrong et al., (1993) J. Mol. Biol. 230, 284-291), removal of these tertiary interactions destabilizes the alpha helix and results in molecules that neither fold nor function in macromolecular recognition (Zondlo & Schepartz, (1999) J. Am. Chem. Soc. 121, 6938-6939). The ability to recapitulate or perhaps even improve on the recognition properties of an alpha helix within the context of a small molecule should find utility in the design of synthetic mimetics or inhibitors of protein function (Cunningham et al., (1997) Curr. Opin. Struct. Biol. 7, 457-462) or new tools for proteomics research.

Two fundamentally different approaches have been taken to bestow alpha helical structure on otherwise unstructured peptide sequences. One approach makes use of modified amino acids or surrogates that favor helix initiation (Kemp et al., (1991) J. Org. Chem. 56, 6683-6697) or helix propagation (Andrews & Tabor, (1999) Tetrahedron 55, 11711-11743; Blackwell & Grubbs, (1998) Angew. Chem. Int. Ed. Eng. 37, 3281-3284; Schafmeister et al., (2000) J. Am. Chem. Soc. 122, 5891-5892). Perhaps the greatest success has been realized by joining the i and i+7 positions of a peptide with a long-range disulfide bond to generate molecules whose helical structure was retained at higher temperatures (Jackson et al., (1991) J. Am. Chem. Soc. 113, 9391-9392). A second approach (Cunningham et al., (1997) Curr. Opin. Struct. Biol. 7,457-462; Nygren, (1997) Curr. Opin. Struct. Biol. 7, 463-469), is to pare the extensive tertiary structure surrounding a given recognition sequence to generate the smallest possible molecule possessing function. This strategy has generated minimized versions of the Z domain of protein A (fifty-nine amino acids) and atrial natriuretic peptide (twenty-eight amino acids). The two minimized proteins, at thirty-three and fifteen amino acids, respectively, displayed high biological activity (Braisted & Wells, (1996) Proc. Natl. Acad. Sci., USA 93, 5688-5692; Li et al., (1995) Science 270, 1657-1660). Despite this success, it is difficult to envision a simple and general application of this truncation strategy in the large number of cases where the alpha helical epitope is stabilized by residues scattered throughout the primary sequence.

In light of this limitation, a more flexible approach to protein minimization called protein grafting has been employed. Schematically, protein grafting involves removing residues required for molecular recognition from their native alpha helical context and grafting them on the scaffold provided by small yet stable proteins. Numerous researchers have engineered protein scaffolds to present binding residues on a relatively small peptide carrier. These scaffolds are small polypeptides onto which residues critical for binding to a selected target can be grafted. The grafted residues are arranged in particular positions such that the spatial arrangement of these residues mimics that which is found in the native protein. These scaffolding systems are commonly referred to as miniproteins. A common feature is that the binding residues are known before the miniprotein is constructed.

Examples of these miniproteins include the thirty-seven amino acid protein charybdotoxin (Vita et al., (1995) Proc. Natl. Acad. Sci. USA 92, 6404-6408; Vita et al., (1998) Biopolymers 47, 93-100) and the thirty-six amino acid protein, avian pancreatic peptide (Zondlo & Schepartz, (1999) Am. Chem. Soc. 121, 6938-6939). Avian pancreatic polypeptide (aPP) is a polypeptide in which residues fourteen through thirty-two form an alpha helix stabilized by hydrophobic contacts with an N-terminal type II polyproline (PPII) helix formed by residues one through eight. Because of its small size and stability, aPP is an excellent scaffold for protein grafting of alpha helical recognition epitopes (Zondlo & Schepartz, (1999) J. Am. Chem. Soc. 121, 6938-6939).

SUMMARY OF THE INVENTION

The invention encompasses an avian pancreatic polypeptide modified by substitution of at least one amino acid residue, this residue being exposed on the alpha helix domain of the polypeptide when the polypeptide is in a tertiary form. In some embodiments, the modified polypeptide contains at least six substituted residues, while in other embodiments it contains eight substituted residues, while in another embodiment it contains ten substituted residues, while in yet another embodiment it contains at least twelve substituted residues.

The substituted residues are selected from any site on a known protein through which interaction with another molecule occurs. Known proteins include, but are not limited to, GCN4, CEBP, Max, Myc, MyoD, double minute two, Bcl-2, protein kinase A, Jun and Fos. In a preferred embodiment, the site on the known protein is a binding site. In some embodiments the modified avian pancreatic polypeptide is capable of inhibiting the interaction between the known protein and another molecule while in other embodiments it is capable of enhancing the interaction. In some embodiments, the binding site is a DNA binding site while in others it is a protein binding site. Preferred DNA binding sites include, but are not limited to the CRE half site, the CEBP site, the MyoD half site and the Q50 engrailed variant site.

The invention also encompasses a phage-display library comprising a plurality of recombinant phage that express any of the aforementioned modified avian pancreatic polypeptides of the invention. In a related embodiment, the invention encompasses a phage-display library comprising a plurality of recombinant phage that express a protein scaffold modified by substitution of at least one amino acid residue, this residue being exposed on the polypeptide when the polypeptide is in a tertiary form. In some embodiments, the protein scaffold of the phage-display library comprises the avian pancreatic polypeptide. The invention also encompasses an isolated phage selected from the phage library of the invention.

The invention further encompasses an isolated polypeptide selected from the group comprising: an isolated polypeptide comprising the amino acid sequence of SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 or 72; an isolated polypeptide comprising a fragment of at least twelve (12) amino acids of SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 or 72; an isolated polypeptide comprising the amino acid sequence of SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 or 72; comprising one or more conservative amino acid substitutions; an isolated polypeptide comprising the amino acid sequence of SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 or 72; comprising one or more naturally occurring amino acid sequence substitutions; and an isolated polypeptide with at least ninety-five (95) percent amino acid homology to SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 or 72. In a related embodiment, the invention also encompasses a nucleic acid encoding any one of the polypeptides aforementioned polypeptides of the invention.

The invention also encompasses a method of preparing a miniprotein that modulates the interaction between a known protein and another molecule, comprising the steps of identifying at least one amino acid residue responsible for the association between a known protein and another molecule; and modifying an avian pancreatic polypeptide by substitution of said at least one amino acid residue, such that it is exposed on the alpha helix domain of the polypeptide when the polypeptide is in a tertiary form.

The invention further encompasses a method of identifying a miniprotein that modulates the interaction between a known protein and another molecule, comprising the step of isolating at least one recombinant phage clone from the phage display library of the invention that displays a protein scaffold that modulates the association between a known protein and another molecule.

BRIEF DESCRIPTION OF THE DRAWINGS

FIG. 4—Seven distinct sequences isolated from BAKLIB phage library. Dissociation constants for miniature protein binding to Bcl-2 are shown on the right. SEQ ID NOs: 22-30 are shown.

FIG. 5—Sequences of the p53 miniature proteins which inhibit p53 binding to hDM2. Residues that stabilize the aPP core are in yellow or blue, residues that contribute to binding hDM2 are in purple, residues identified by phage display are in red. Equilibrium dissociation constants of stable $PPBR^{SR}$-hsCRE complexes are listed at right. SEQ ID NOs: 31-37 are shown. The aPP sequence comprises residues 1-31 of SEQ ID NO: 6.

DETAILED DESCRIPTION

Definitions

As used herein, the term "binding" refers to the specific association or other specific interaction between two molecular species, such as, but not limited to, protein-DNA interactions and protein-protein interactions. For examples, the specific association between proteins and their DNA targets, receptors and their ligands, enzymes and their substrates. It is contemplated that such association is mediated through specific sites on each of the two interacting molecular species. Binding is mediated by structural and/or energetic components, the latter comprising the interaction of molecules with opposite charges.

As used herein, the term "binding site" refers to the reactive region or domain of a macromolecule that directly participate in its specific binding with another molecule. For example, when referring to the binding site on a protein or nucleic acid, binding occurs as a result of the presence of specific amino acids or nucleotide sequence, respectively, that interact with the other molecule and, collectively, are referred to as a "binding site."

As used herein, the term "exposed on the alpha helix domain" means that an amino acid substituted, for example, into the avian pancreatic polypeptide is available for association or interaction with another molecule and are not otherwise bound to or associated with another amino acid residue on the avian pancreatic polypeptide. This term is used interchangeably with the term "solvent-exposed alpha helical face" throughout the specification.

As used herein, the terms "miniature protein" or "miniprotein" refers to a relatively small protein containing at least a protein scaffold and one or more additional domains or regions that help to stabilize its tertiary structure.

As used herein, the term "modulate" refers to an alteration in the association between two molecular species, for example, the effectiveness of a biological agent to interact with its target by altering the characteristics of the interaction in a competitive or non-competitive manner.

As used herein, the term "protein" refers to any of a group of complex organic compounds which contain carbon, hydrogen, oxygen, nitrogen and usually sulphur, the characteristic element being nitrogen and which are widely distributed in plants and animals. Twenty different amino acids are commonly found in proteins and each protein has a unique, genetically defined amino acid sequence which determines its specific shape and function. The term "protein" is generally used herein interchangeably with the terms peptide and polypeptide.

As used herein, the term "protein scaffold" refers to a region or domain of a relatively small protein, such as a miniature protein, that has a conserved tertiary structural motif which can be modified to display one or more specific amino acid residues in a fixed conformation.

Miniature Proteins

Figure 1:
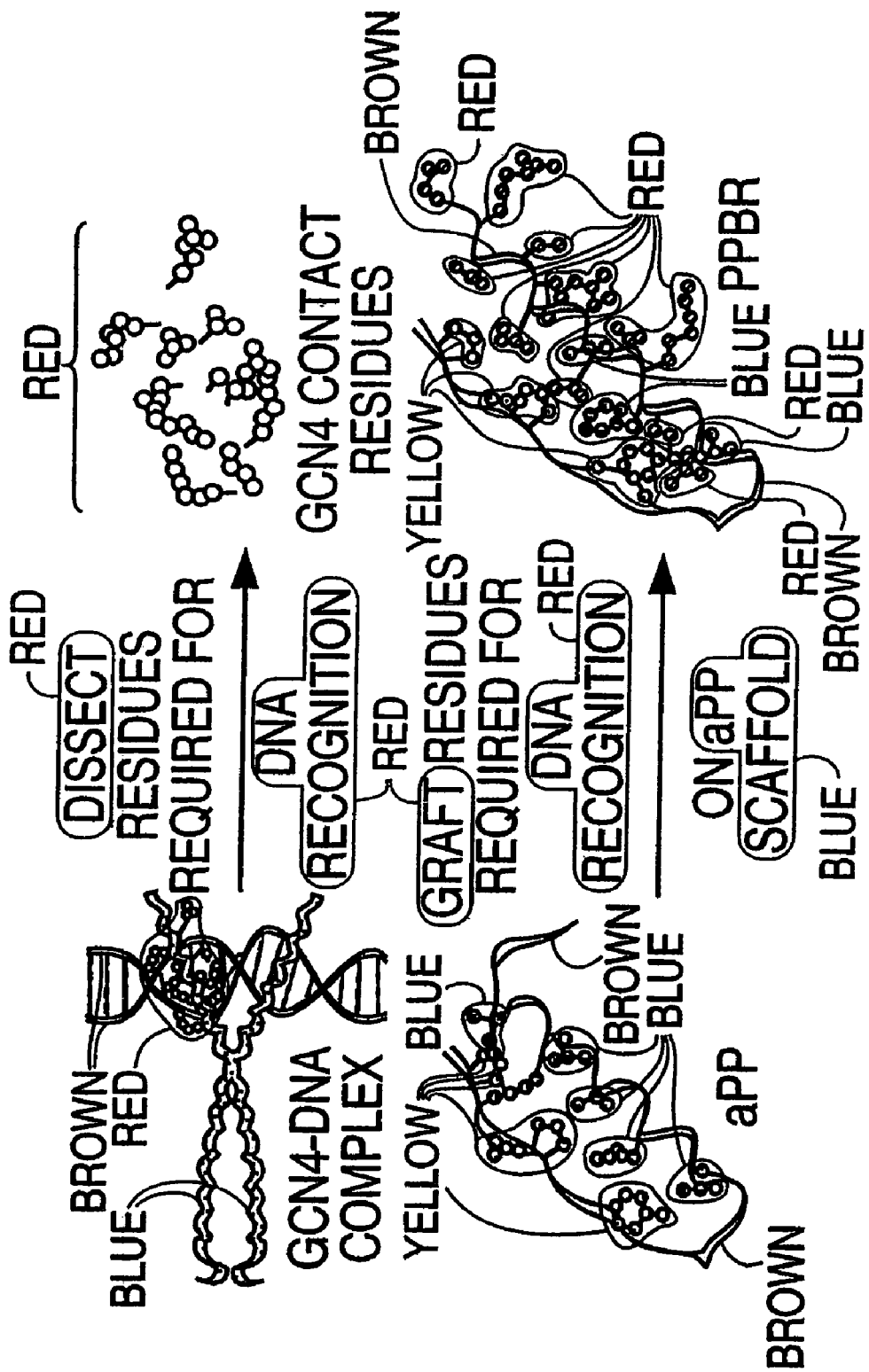
FIG. 1—Protein grafting strategy for the design of DNA-binding miniature proteins.

The present invention provides engineered miniature proteins that associate with (i.e., or bind to) specific sequences of DNA or other proteins and also provides methods for designing and making these miniature proteins. These miniature proteins bind, for example, to DNA or other proteins with high affinity and selectivity. Schematically, the invention involves a technique that the inventors have designated as protein grafting (see, e.g., FIG. 1). In one aspect, this technique identifies critical binding site residues from a globular protein that participate in binding-type association between that protein and its specific binding partners, then these residues are grafted onto a small but stable protein scaffold. The preferred protein scaffolds of the invention comprise members of the pancreatic fold (PP fold) protein family, particularly the avian pancreatic polypeptide.

The PP fold protein scaffolds of the invention generally contain thirty-six amino acids and are the smallest known globular proteins. Despite their small size, PP fold proteins are stable and remain folded under physiological conditions. The preferred PP fold protein scaffolds of the invention consist of two anti-parallel helices, an N-terminal type II polyproline helix (PPII) between amino acid residues two and eight and an alpha-helix between residues 14 and 31 and/or 32. The stability of the PP fold protein scaffolds of the invention derives predominantly from interactions between hydrophobic residues on the interior face of the alpha-helix at positions 17, 20, 24, 27, 28, 30 & 31 and the residues on the two edges of the polyproline helix at positions 2, 4, 5, 7 & 8. In general, the residues responsible for stabilizing it tertiary structure are not substituted in order to maintain the tertiary structure of the miniature protein or are compensated for using phage display.

In certain embodiments, two or more of the critical binding site residues of, for example, a selected globular protein are grafted onto the protein scaffold in positions which are not essential in maintaining tertiary structure, preferably on the solvent-exposed alpha helical face. In one preferred embodiment, six or more of such binding site residues are grafted onto the protein scaffold. In a more preferred embodiment, eight or more of such binding site residues are grafted onto the protein scaffold. In an even more preferred embodiment, ten or more of such binding site residues are grafted onto the protein scaffold. In a most preferred embodiment, twelve or more of such binding site residues are grafted onto the protein scaffold. Preferred positions for grafting these binding site residues on the protein scaffold include, but are not limited to, positions on the solvent-exposed alpha-helical face of aPP. Substitutions of binding site residues may be made, although they are less preferred, for residues involved in stabilizing the tertiary structure of the miniature protein.

The skilled artisan will readily recognize that it is not necessary that actual substitution of the grafted residues occur on the protein scaffold. Rather it is necessary that a peptide be identified, through, for example, phage display, that comprises a polypeptide constituting a miniature protein having the association characteristics of the present invention. Such peptides may be produced using any conventional means, including, but not limited to synthetic and recombinant techniques.

Members of the PP fold family of protein scaffolds which are contemplated by the present invention include, but are not limited to, avian pancreatic polypeptide (aPP), Neuropeptide Y, lower intestinal hormone polypeptide and pancreatic peptide. In the most preferred embodiment, the protein scaffold comprises the PP fold protein, avian pancreatic polypeptide (SEQ ID NO: 06) (see, e.g., Blundell et al., (1981) Proc. Natl. Acad. Sci. USA 78, 4175-4179; Tonan et al., (1990) Biochemistry 29, 4424-4429). aPP is a PP fold polypeptide characterized by a short (eight residue) amino-terminal type II polyproline helix linked through a type I beta turn to an eighteen residue alpha-helix. Because of its small size and stability, aPP is an excellent protein scaffold for, e.g., protein grafting of alpha-helical recognition epitopes.

DNA-binding Miniature Proteins

In another aspect, the present invention encompasses miniature proteins that bind to specific DNA sequences and further encompasses methods for making and using such miniature proteins. In some embodiments, these DNA sequences comprise sites for known proteins that bind to that specific DNA sequence (contemplated known proteins would be, e.g., a promotor or regulator). For example, in the design of a DNA-binding miniature protein, the amino acid residues of a known protein that participate in binding or other association of the protein to that particular DNA sequence are identified.

In some embodiments of the present invention, the relevant binding residues are identified using three-dimensional models of a protein or protein complex based on crystallographic studies while in other embodiments they are identified by studies of deletion or substitution mutants of the protein. The residues that participate in binding of the protein to the specific DNA sequence are then grafted onto those positions of the miniature protein that are not necessary to maintain the tertiary structure of the protein scaffold to form the DNA-binding miniature protein. The identification of such positions can readily be determined empirically by persons skilled in the art. Other embodiments of the present invention involve the screening of a library of modified miniproteins that contain peptide species capable of specific association or binding to that specific DNA (or, in other cases, protein) sequence or motif.

Generally, it is contemplated that any potential binding site on a DNA sequence can be targeted using the DNA binding miniature proteins of the invention. Preferred embodiments include helical structures which bind to the DNA binding site. In some embodiments, the binding involves a basic region leucine zipper (bZIP) structure (Konig & Richmond, (1995) J. Mol. Biol. 254, 657-667) while in other embodiments the structure involves a basic-helix-loop-helix (bHLH) structure (Shimizu et al., (1997) EMBO J. 16, 4689-4697). In another embodiment, the binding involves a structure like those found in homeodomain proteins (Scott & Weimer, (1984) Proc. Natl. Acad. Sci. 81, 4115-4119). Preferred bZIP structures include, but are not limited to, those found in GCN4 and C/EBP-delta (Suckow et al., (1993) EMBO J. 12, 1193-1200) while preferred bHLH structures include, but are not limited to, those found in Max (Ferre-D'Amare et al., (1993) Nature 363, 38-45), Myc and MyoD (Ma et al., (1994) Cell 77, 451-459). Preferred homeodomain structures include, but are not limited to, those found in the Q50 engrailed variant protein (Kissinger et al., (1990) Cell 63, 579-590).

Figure 2:
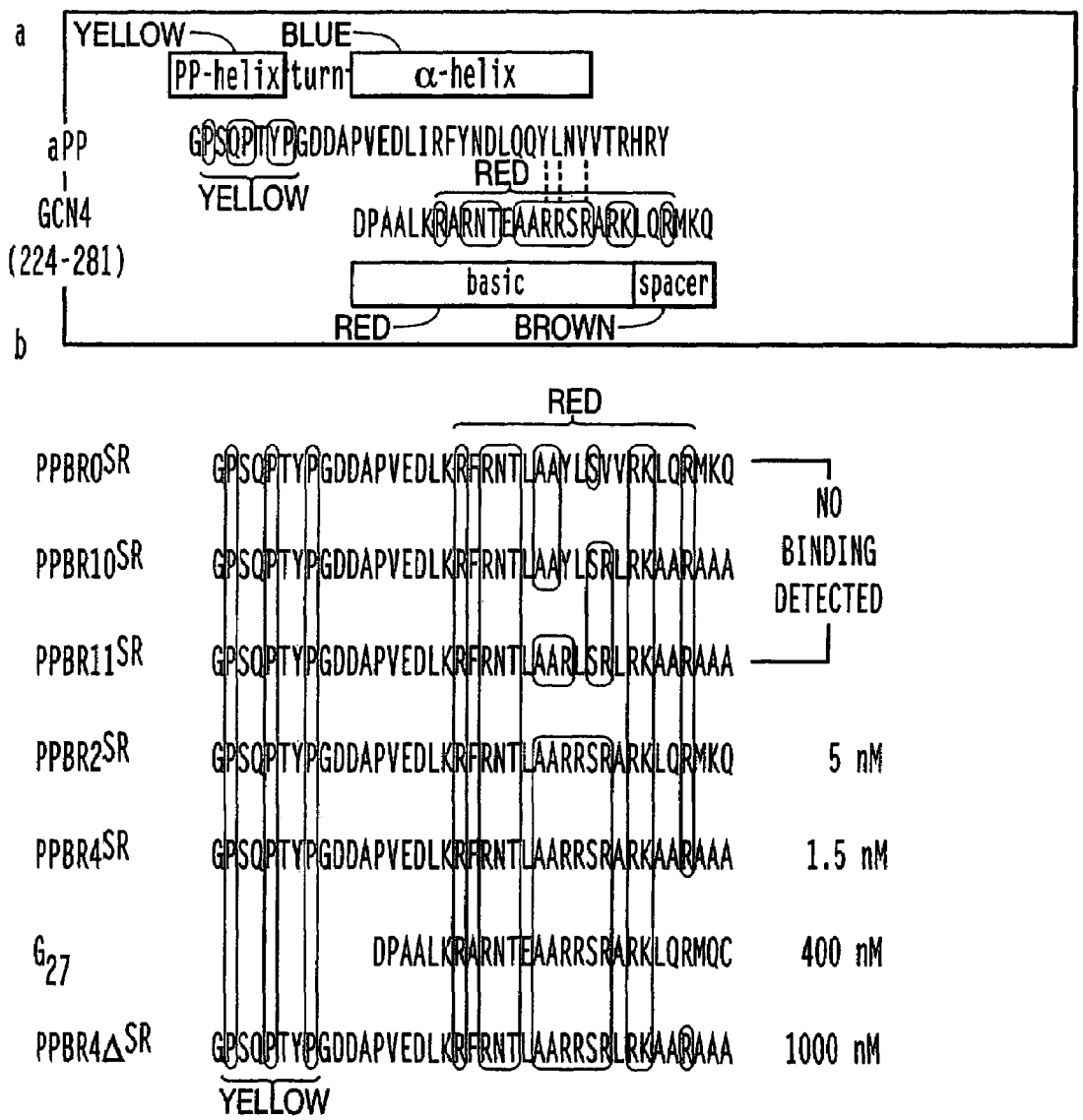
FIG. 2—(A) Alignment of the aPP and the GCN4 basic-spacer segment sequences used to guide protein design. Essential DNA-contact residues within GCN4 are in pink; essential folding residues within aPP are in yellow or blue. Conflict positions are indicated by a dashed line. (B) Peptides used and their affinities for hsCRE24. Equilibrium dissociation constants of stable $PPBR^{SR}$-hsCRE complexes are listed at right. All peptides except $G_{56}$ and $G_{27}$ contained GGC sequences at their carboxyl termini. $G_{27}$ contained a single cysteine. The carboxy-terminal cysteine was alkylated with bromoacetamide to study protein monomers (PP-$BR^{SR}$ & $G_{27}$) or oxidized to study disulfide-linked dimers ($PPBR^{SS}$). SEQ ID NOs: 6-14 are shown.

In one embodiment, the invention encompasses a DNA-binding miniature protein that binds to the cAMP Response Element (CRE) half-site promotor DNA sequence (ATGAC) (SEQ ID NO: 65). Essential residues for binding are identified from the protein GCN4 which is a bZIP protein which binds to this sequence. These residues are identified by utilizing the three-dimensional structure of the GCN4 protein which bind to the hsCRE and grafting these residues onto the protein scaffold. By grafting various combinations of residues on the solvent-exposed alpha-helical face or domain of aPP which are essential to binding of GCN4 (SEQ ID NO: 7) to the CRE half site (hsCRE), a series of polyproline helix-basic region (PPBR$^{SR}$) molecules containing most or all of the DNA-contact residues of GCN4 and most or all of the folding residues of aPP is generated (FIG. 2). This procedure generated three positions (Tyr27, Leu28 and Val30) where essential DNA-contact and aPP-folding residues occupied a single position on the helix (FIG. 2).

Examples of the DNA-binding miniature proteins which bind to hsCRE include, but are not limited to, the amino acid sequences depicted in SEQ ID NO: 11 (PPBR2$^{SR}$), 12 (PPBR4$^{SR}$), 13 (G$_{27}$) & 14 (PPBR4$\Delta^{SR}$).

In another embodiment, protein grafting was used for the design of a miniature protein whose DNA binding properties mimic those of the CCAAT/enhancer protein C/EBP-delta. C/EBP-delta is a member of the C/EBP sub-family of bZIP transcription factors that includes C/EBP-alpha, C/EBP-beta, C/EBP-gamma, C/EBP-delta and C/EBP-epsilon. Although C/EBP proteins are members of the bZIP superfamily, they differ from CGN4 at several residues within the DNA recognition helix. In particular, D/EBP-delta and GCN4 differ at two of six residues that contact bases or sugars and three of six residues that contact phosphates in all published structures of GCN4 DNA complexes. These changes, as well as the substitution of tyrosine or alanine at position fifteen, contribute to the preferred interaction of C/EBP proteins with the C/EBP site (ATTGCGCAAT) (SEQ ID NO: 67) over the CRE site (ATGACGTCAT) (SEQ ID NO: 68) recognized by GCN4.

For the design of PPEBP (polyproline-enhancer binding protein) according to the present invention, the first step in the grafting protocol is alignment of the alpha-helix of aPP (residues 14-36) with the alpha-helical region of the protein of interest. Alignment of the aPP alpha-helix with residues 187-221 (the DNA-binding basic segment) of human C/EBP-delta identified three conflict positions (27, 28 & 30 according to the aPP numbering system) where DNA-contact residues within C/EBP-delta and folding residues within aPP occupied the same position on the helix. The PPEBP1$^{SR}$ (SEQ ID NO: 47) miniature protein of the invention contains arginine residues derived from C/EBP-delta at positions 27, 28 & 30 to preserve binding affinity because high-affinity DNA recognition by PPEBP miniature proteins is enhanced by retention of DNA-contact residues at these positions despite the concomitant loss in folding energy. In addition, tyrosine, asparagine and valine residues are substituted at positions 15, 23 & 26, respectively to foster specific recognition of the C/EBP half site ATTGC (hs-CEBP). Finally an alanine residue is inserted at position 31 in place of the potentially core-disrupting and complex-destabilizing aspartate found in C/EBP-delta and in place of the helix destabilizing valine present at this position of aPP.

Examples of the DNA-binding miniature proteins which bind to the C/EBP site include, but are not limited to, the amino acid sequences depicted in SEQ ID NO: 47 (PPEBP1$^{SR}$), 48 (PPEBP2$^{SR}$) and 49 (EBP1$^{SR}$).

Production of Miniature Proteins using Phage Display

In some embodiments, a miniature protein is produced and selected using a phage display method (McCafferty et al., (1990) Nature 348, 552-554). In such a method, display of recombinant miniature proteins on the surface of viruses which infect bacteria (bacteriophage or phage) make it possible to produce soluble, recombinant miniature proteins having a wide range of affinities and kinetic characteristics. To display the miniature proteins on the surface of phage, a synthetic gene encoding the miniature protein is inserted into the gene encoding a phage surface protein (pIII) and the recombinant fusion protein is expressed on the phage surface (McCafferty et al., (1990) Nature 348, 552-554; Hoogenboom et al., (1991) Nucleic Acids Res. 19, 4133-4137). Variability is introduced into the phage display library to select for miniature proteins which not only maintain their tertiary, helical structure but which also display increased affinity for a preselected target because the critical (or contributing but not critical) binding residues are optimally positioned on the helical structure.

Since the recombinant proteins on the surface of the phage are functional, phage bearing miniature proteins that bind with high-affinity to a particular target DNA or protein can be separated from non-binding or lower affinity phage by antigen affinity chromatography. Mixtures of phage are allowed to bind to the affinity matrix, non-binding or lower affinity phage are removed by washing, and bound phage are eluted by treatment with acid or alkali. Depending on the affinity of the miniature protein for its target, enrichment factors of twenty-fold to a million-fold are obtained by a single round of affinity selection. By infecting bacteria with the eluted phage, however, more phage can be grown and subjected to another round of selection. In this way, an enrichment of a thousand-fold in one round becomes a million-fold in two rounds of selection. Thus, even when enrichments in each round are low (Marks et al., (1991) J. Mol. Biol, 222, 581-597), multiple rounds of affinity selection leads to the isolation of rare phage and the genetic material contained within which encodes the sequence of the domain or motif of the recombinant miniature protein that binds or otherwise specifically associates with it binding target.

In various embodiments of the invention, the methods disclosed herein are used to produce a phage expression library encoding miniature proteins capable of binding to a DNA or to a protein that has already been selected using the protein grafting procedure described above. In such embodiments, phage display can be used to identify miniature proteins that display an even higher affinity for a particular target DNA or protein than that of the miniature proteins produced without the aid of phage display. In yet another embodiment, the invention encompasses a universal phage display library that can be designed to display a combinatorial set of epitopes or binding sequences to permit the recognition of nucleic acids, proteins or small molecules by a miniature protein without prior knowledge of the natural epitope or specific binding residues or motifs natively used for recognition and association.

Various structural modifications also are contemplated for the present invention that, for example, include the addition of restriction enzyme recognition sites into the polynucleotide sequence encoding the miniature protein that enable genetic manipulation of these gene sequences. Accordingly, the re-engineered miniature proteins can be ligated, for example, into an M13-derived bacteriophage cloning vector that permits expression of a fusion protein on the phage surface. These methods allow for selecting phage clones encoding fusion proteins that bind a target ligand and can be completed in a rapid manner allowing for high-throughput screening of miniature proteins to identify the miniature protein with the highest affinity and selectivity for a particular target.

According to the methods of the invention, a library of phage displaying modified miniature proteins is incubated with the immobilized target DNA or proteins to select phage clones encoding miniature proteins that specifically bind to or otherwise specifically associate with the immobilized DNA or protein. This procedure involves immobilizing a oligonucleotide or polypeptide sample on a solid substrate. The bound phage are then dissociated from the immobilized oligonucleotide or polypeptide and amplified by growth in bacterial host cells. Individual viral plaques, each expressing a different recombinant miniature protein, are expanded to produce amounts of protein sufficient to perform a binding assay. The DNA encoding this recombinant binding protein can be subsequently modified for ligation into a eukaryotic protein expression vector. The modified miniature protein, adapted for expression in eukaryotic cells, is ligated into a eukaryotic protein expression vector.

Phage display methods that can be used to make the miniature proteins of the present invention include those disclosed in Brinkman et al., (1995) J. Immunol. Methods 182, 41-50; Ames et al., (1995) J. Immunol. Methods 184:177-186; Kettleborough et al., (1994) Eur. J. Immunol. 24, 952-958; Persic et al., (1997) Gene 187, 9-18; Burton et al., (1994) Adv. Immunol. 57, 191-280; U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743, 5,837,500 & 5,969,108.

Protein-Binding Miniature Proteins

The invention encompasses miniature proteins that bind to other proteins and methods for making these miniature proteins. The binding of the miniature proteins modulates protein-protein and/or protein-ligand interactions. Thus, in some embodiments the binding blocks the association (or specific binding) of ligands and receptors. The ligand can be either another protein but also can be any other type of molecule such as a chemical substrate. In one embodiment of the present invention, making the protein-binding miniature protein of the invention involves identifying the amino acid residues which are essential to binding of the ligand protein to its target receptor protein. In some embodiments, these essential residues are identified using three-dimensional models of a protein or protein complex which binds to or interacts with another protein based on crystallographic studies while in other embodiments they are identified by studies of deletion or substitution mutants of the protein. The residues that participate in binding of the protein to are then grafted onto those positions which are not necessary to maintain the tertiary structure of the protein scaffold to form the protein-binding miniature protein.

The structure of any protein which binds to another protein can be used to derive the protein-binding miniature proteins of the invention. Preferred embodiments include helical structures such as those involved in protein-protein interactions between Fos and Jun (Kouzarides & Ziff, (1988) Nature 336, 646-651), Bcl-2 and Bak (Sattler et al., (1997) Science 275, 983-986), CBP-KIX and CREB-KID (Radhakrishnan et al., (1997) Cell 91, 741-752) and p53 binding to DM2 (Kussie et al., (1996) Science 274, 948-953). In some embodiments, the binding involves coiled coil protein structures and/or leucine zippers.

In one embodiment of the invention, the methods disclosed herein are used to produce a miniature protein that binds to the Bcl-2 or Bcl-$X_L$ proteins (Sattler et al., (1997) Science 275, 983-986). In this method, the protein grafting procedure described herein was applied to the Bak-BH3 binding domain to design a miniature protein capable of binding to Bcl-$X_L$. In this procedure, the primary sequence of a protein of interest is aligned with residues in the alpha helix of aPP. All possible alignments of the primary sequence of positions 74-92 of Bak with aPP are assessed in two ways. First, the number of conflicts in a primary sequence alignment between residues important for hydrophobic core formation or maintenance of aPP helix dipole, and residues in Bak important for binding Bcl-$X_L$ was considered. Alignments with a large number of conflicts are eliminated as they would force selection between sequences that were well folded or have high affinity, but make it difficult to isolate a molecule with both these properties.

Structural models of the aPP based peptides that are associated or complexed with the BH3 domain of Bcl-$X_L$ in each of the alignments are evaluated for unfavorable interactions or steric clashes between the VanderWaals surface of Bcl-$X_L$ and the backbone of the aPP scaffold. Structural models with multiple unfavorable interactions or steric clashes are eliminated from further consideration.

An alignment is identified with only a single conflict where structural modeling suggested no steric clashes. A phage display expression library of chimeric peptides ultimately was based on this alignment. The resulting library of peptides was displayed on the surface of M13 phage and used in selection and isolation of miniature proteins that bind Bcl with high-affinity. Examples of the protein-binding miniature proteins isolated from the phage display library which bind to Bcl include, but are not limited to, the amino acid sequences depicted in SEQ ID NO: 23 (4100), 24 (4101), 25 (4099) & 26 (4102).

In another embodiment of the invention, the methods of the invention are used to produce a miniature protein that binds to the human oncoprotein double minute two (hDM2). The alpha-helical segments of p53 and aPP were aligned to identify three critical hDM2 contact residues (positions 22, 26 & 29) on the exposed alpha-helical face of aPP without substituting any aPP residues important for folding. Because many p53 residues within the p53 activation domain that interacts with hDM2 display phi and psi angles outside the ideal alpha-helical range, this application of protein grafting introduced diversity at five positions along the alpha-helix and the highest affinity ligands were selected using phage display.

Examples of the protein-binding miniature proteins isolated from the phage display library which bind to hDM2 include, but are not limited to, the amino acid sequences depicted in SEQ ID NO: 31 (p53AD), 33 (p3254), 34 (p3255), 35 (p3548), 36 (p3559) & 37 (p3257).

Miniature Protein Variants

The miniature proteins of the present invention further include conservative variants of the miniature proteins herein described. As used herein, a conservative variant refers to alterations in the amino acid sequence that do not substantially and adversely affect the binding or association capacity of the protein. A substitution, insertion or deletion is said to adversely affect the miniature protein when the altered sequence prevents or disrupts a function or activity associated with the protein. For example, the overall charge, structure or hydrophobic-hydrophilic properties of the miniature protein can be altered without adversely affecting an activity. Accordingly, the amino acid sequence can be altered, for example to render the peptide more hydrophobic or hydrophilic, without adversely affecting the activities of the miniature protein.

These variants, though possessing a slightly different amino acid sequence than those recited above, will still have the same or similar properties associated with the miniature proteins depicted in SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 or 72.

Ordinarily, the conservative substitution variants, will have an amino acid sequence having at least ninety percent amino acid sequence identity with the miniature sequences set forth in SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 or 72, more preferably at least ninety-five percent, even more preferably at least ninety-eight percent, and most preferably at least ninety-nine percent. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the miniature proteins of the present invention include molecules comprising the amino acid sequence of SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 or 72; fragments thereof having a consecutive sequence of at least about 20, 25, 30, 35 or more amino acid residues of the miniature proteins of the invention; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those derivatives wherein the protein has been covalently modified by substitution, chemical, enzymatic, or other appropriate means with a moiety other than a naturally occurring amino acid (for example, a detectable moiety such as an enzyme or radioisotope).

Nucleic Acid Molecules Encoding Miniature Proteins

The present invention further provides nucleic acid molecules that encode the miniature proteins comprising the amino acid sequence of SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 or 72 and the related miniature proteins herein described, preferably in isolated form. As used herein, "nucleic acid" includes cDNA and mRNA, as well as nucleic acids based on alternative backbones or including alternative bases whether derived from natural sources or synthesized.

As used herein, a nucleic acid molecule is said to be "isolated" when the nucleic acid molecule is substantially separated from contaminant nucleic acid encoding other polypeptides from the source of nucleic acid.

The present invention further provides fragments of the encoding nucleic acid molecule. As used herein, a "fragment of an encoding nucleic acid molecule" refers to a portion of the entire protein encoding sequence of the miniature protein. The size of the fragment will be determined by the intended use. For example, if the fragment is chosen so as to encode an active portion of the protein, the fragment will need to be large enough to encode the functional region(s) of the protein. The appropriate size and extent of such fragments can be determined empirically by persons skilled in the art.

Modifications to the primary structure itself by deletion, addition, or alteration of the amino acids incorporated into the protein sequence during translation can be made without destroying the activity of the miniature protein. Such substitutions or other alterations result in miniature proteins having an amino acid sequence encoded by a nucleic acid falling within the contemplated scope of the present invention.

The present invention further provides recombinant DNA molecules that contain a coding sequence. As used herein, a recombinant DNA molecule is a DNA molecule that has been subjected to molecular manipulation. Methods for generating recombinant DNA molecules are well known in the art, for example, see Sambrook et al., (1989) Molecular Cloning—A Laboratory Manual, Cold Spring Harbor Laboratory Press. In the preferred recombinant DNA molecules, a coding DNA sequence is operably linked to expression control sequences and vector sequences.

The choice of vector and expression control sequences to which one of the protein family encoding sequences of the present invention is operably linked depends directly, as is well known in the art, on the functional properties desired (e.g., protein expression, and the host cell to be transformed). A vector of the present invention may be at least capable of directing the replication or insertion into the host chromosome, and preferably also expression, of the structural gene included in the recombinant DNA molecule Expression control elements that are used for regulating the expression of an operably linked miniature protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extra-chromosomal in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical of bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Any suitable prokaryotic host can be used to express a recombinant DNA molecule encoding a protein of the invention.

Expression vectors compatible with eukaryotic cells, preferably those compatible with vertebrate cells, can also be used to form a recombinant DNA molecules that contains a coding sequence. Eukaryotic cell expression vectors are well known in the art and are available from several commercial sources. Typically, such vectors are provided containing convenient restriction sites for insertion of the desired DNA segment.

Eukaryotic cell expression vectors used to construct the recombinant DNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., (1982) J. Mol. Anal. Genet. 1, 327-341). Alternatively, the selectable marker can be present on a separate plasmid, the two vectors introduced by co-transfection of the host cell, and transfectants selected by culturing in the appropriate drug for the selectable marker.

Transformed Host Cells

The present invention further provides host cells transformed with a nucleic acid molecule that encodes a miniature protein of the present invention The host cell can be either prokaryotic or eukaryotic. Eukaryotic cells useful for expression of a miniature protein of the invention are not limited, so long as the cell line is compatible with cell culture methods and compatible with the propagation of the expression vector and expression of the gene product.

Transformation of appropriate cell hosts with a recombinant DNA molecule encoding a miniature protein of the present invention is accomplished by well known methods that typically depend on the type of vector used and host system employed. With regard to transformation of prokaryotic host cells, electroporation and salt treatment methods can be employed (see, for example, Sambrook et al., (1989) Molecular Cloning—A Laboratory Manual, Cold Spring Harbor Laboratory Press; Cohen et al., (1972) Proc. Natl. Acad. Sci. USA 69, 2110-2114). With regard to transformation of vertebrate cells with vectors containing recombinant DNA, electroporation, cationic lipid or salt treatment methods can be employed (see, for example, Graham et al., (1973) Virology 52, 456-467; Wigler et al., (1979) Proc. Natl. Acad. Sci. USA 76, 1373-1376).

Successfully transformed cells (cells that contain a recombinant DNA molecule of the present invention), can be identified by well known techniques including the selection for a selectable marker. For example, cells resulting from the introduction of a recombinant DNA of the present invention can be cloned to produce single colonies. Cells from those colonies can be harvested, lysed and their DNA content examined for the presence of the recombinant DNA using a method such as that described by Southern, (1975) J. Mol. Biol. 98, 503-517 or the proteins produced from the cell assayed via an immunological method.

Production of Recombinant Miniature Proteins

The present invention further provides methods for producing a miniature protein of the invention using nucleic acid molecules herein described. In general terms, the production of a recombinant form of a protein typically involves the following steps: a nucleic acid molecule is obtained that encodes a protein of the invention, such as the nucleic acid molecule encoding any of the miniature proteins depicted in SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 or 72. The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant miniature protein. Optionally the recombinant miniature protein is isolated from the medium or from the cells; recovery and purification of the protein may not be necessary in some instances where some impurities may be tolerated.

Each of the foregoing steps can be done in a variety of ways. The construction of expression vectors that are operable in a variety of hosts is accomplished using appropriate replicons and control sequences, as set forth above. The control sequences, expression vectors, and transformation methods are dependent on the type of host cell used to express the gene. Suitable restriction sites, if not normally available, can be added to the ends of the coding sequence so as to provide an excisable gene to insert into these vectors. A skilled artisan can readily adapt any host/expression system known in the art for use with the nucleic acid molecules of the invention to produce a recombinant miniature protein.

Methods to Identify Binding Partners

The present invention provides methods for use in isolating and identifying binding partners of the miniature proteins of the invention. In some embodiments, a miniature protein of the invention is mixed with a potential binding partner or an extract or fraction of a cell under conditions that allow the association of potential binding partners with the protein of the invention. After mixing, peptides, polypeptides, proteins or other molecules that have become associated with a miniature protein of the invention are separated from the mixture. The binding partner bound to the protein of the invention can then be removed and further analyzed. To identify and isolate a binding partner, the entire miniature protein can be used. Alternatively, a fragment of the miniature protein which contains the binding domain can be used.

As used herein, a "cellular extract" refers to a preparation or fraction which is made from a lysed or disrupted cell. A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the a miniature protein of the invention under conditions in which association of the miniature protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density-sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the miniature protein of the invention can be immobilized on a solid support. For example, the miniature protein can be attached to a nitrocellulose matrix or acrylic beads. Attachment of the miniature protein to a solid support aids in separating peptide-binding partner pairs from other constituents found in the extract. The identified binding partners can be either a single DNA molecule or protein or a complex made up of two or more proteins. Alternatively, binding partners may be identified using the Alkaline Phosphatase fusion assay according to the procedures of Flanagan & Vanderhaeghen, (1998) Annu. Rev. Neurosci. 21, 309-345 or Takahashi et al., (1999) Cell 99, 59-69; the Far-Western assay according to the procedures of Takayama et al., (1997) Methods Mol. Biol. 69, 171-184 or Sauder et al., J. Gen. Virol. (1996) 77, 991-996 or identified through the use of epitope tagged proteins or GST fusion proteins.

Alternatively, the nucleic acid molecules encoding a miniature protein of the invention can be used in a yeast two-hybrid system. The yeast two-hybrid system has been used to identify other protein partner pairs and can readily be adapted to employ the nucleic acid molecules herein described (see, e.g., Stratagene Hybrizap® two-hybrid system).

Screening, Diagnostic & Therapeutic Uses

The miniature proteins of the invention are particularly useful for drug screening to identify agents capable of binding to the same binding site as the miniature proteins. The miniature proteins are also useful for diagnostic purposes to identify the presence and/or detect the levels of DNA or protein that binds to the miniature proteins of the invention. In one diagnostic embodiment, the miniature proteins of the invention are included in a kit used to detect the presence of a particular DNA or protein in a biological sample. The miniature proteins of the invention also have therapeutic uses in the treatment of disease associated with the presence of a particular DNA or protein. In one therapeutic embodiment, the miniature proteins can be used to bind to DNA to promote or inhibit transcription, while in another therapeutic embodiment, the miniature proteins bind to a protein resulting in inhibition or stimulation of the protein.

Without further description, it is believed that a person of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Synthesis of DNA-Binding Miniature Proteins

Polypeptides constituting miniature proteins were prepared using solid phase methodology and contain a carboxy-terminal amide and a free amino terminus unless otherwise indicated. High performance liquid chromatography (HPLC) was performed on either a Waters 600E Multisolvent Delivery System with a Waters 490E multiwavelength detector or a Rainin Dynamax SD-200 Solvent Delivery System with a Rainin Dynamax PDA-2 Diode Array Detector.

Solid phase peptide synthesis was performed on a Perseptive BioSearch 9600 peptide synthesizer. Standard research grade argon (Connecticut AirGas) was passed through an OxyClear oxygen scrubber before introduction to the synthesizer. HATU (O-(7-benzotrizol-1-yl)-1,1,3,3,-tetramethyl uronium hexafluorophosphate) was used as the activating reagent without addition of supplemental benzotrizole. Dimethylformamide, piperidine and methylene chloride (Baker) were fresh and stored under nitrogen. Anhydrous dimethylformamide was mixed with diisopropylethylamine (DIPEA, redistilled 0.46 M) to prepare the base activator solution. 9-Fluorenylmethoxycarbonyl (F-moc)-protected amino acids utilized the following side chain protecting groups: O-t-butyl (Asp, Glu); t-butyl (Tyr, Thr, Ser); 2,2,4,6,7-pentamethyldihydrobenzofuran-5-sulfonyl (Pbf) (Arg); t-butoxycarbonyl (Lys); and triphenylmethyl (Cys, His, Asn, Gln). Synthesis was performed on a 0.10 mmol scale using PAL (peptide amide linker) resin (Fmoc-$NH_2$—$CH_2$-(di-m-methoxy,p-O-$(CH_2)_4$C(O)-polystyrene) which resulted in an amidated carboxy-terminus. Fmoc-amino acid and HATU were used in four-fold excess (0.4 mmol per coupling). After the final coupling was completed, the Fmoc-protecting group was removed and the resin was washed for the last time. The resin was dried and stored in a desicator until cleavage and deprotection were initiated.

Reverse phase HPLC was performed using eluents composed of mixtures of Buffer A (98% HPLC water, 2% acetonitrile, 0.05% trifluoroacetic acid) and Buffer B (20% HPLC water, 80% acetonitrile, 0.06% trifluoroacetic acid). All HPLC solvents were filtered through a 0.2 micron filter prior to use. Solvents and chemicals for peptide synthesis were obtained from Aldrich and Perseptive Biosearch unless stated otherwise. Peptides were lyophilized using a Savant SC100 Speed Vacuum instrument. Denaturing sodium dodecyl sulfate-polyacryalmide gel electrophoresis (SDS-PAGE) analysis was performed with a Pharmacia PhastGel system using High Density gels (20% acrylamide soaked in glycerol). Amino acid analysis was assayed on a Beckman Analyzer.

For deprotection and purification of PPEBP1$^{SH}$, PAL resin (15 mg) containing protected PPEBP1$^{SH}$ was allowed to react for five hours at room temperature in a deprotection cocktail (84% trifluoroacetic acid, 4% phenol, 4% ethanedithiol, 4% thioanisole and 4% water). The solvent was removed by blowing a stream of nitrogen over the solution until the volume reached approximately 0.25 ml. Diethylether (1 ml) and dithiothreitol (20 mg) were added to precipitate the peptide and stabilize the cysteine. The supernatant was removed after centrifugation and the precipitate dried. The crude peptide was dissolved in 1 ml phosphate-buffered saline (pH 7.5) with added dithiothreitol (5 mg) and filtered with a 0.2 micron filter. The peptide was purified by reverse phase HPLC (Vydac semipreparative 300 Å C18, 5 microns, 10.0×250 mm) using a 120 minute linear gradient of 100-30% Buffer A in Buffer B. The peptide eluted at 49.3 minutes using a flow rate of 4 ml/min and was analyzed by electrospray ionization mass spectrometry. The predicted and observed masses were 4729.4 and 4730.0, respectively.

For preparation of PPEBP1$^{SR}$, 0.080 mg of PPEBP1$^{SH}$ was dissolved in 0.50 ml of 2 mg/ml (15 mM) 2-bromoacetamide in 20 mM sodium phosphate buffer (pH 7.5). The reaction was allowed to proceed for thirty minutes at room temperature. The peptide was purified by reverse phase HPLC (Rainin analytical 100 Å C18, 5 microns, 4.6×250 mm) using a forty minute linear gradient of 100-30% Buffer A in Buffer B. The peptide eluted at 23.3 minutes using a flow rate of 1 ml/min and was characterized by electrospray ionization mass spectrometry and amino acid analysis. AAA expected: Ala5 Asx5 CmCys1 Glx2 Phe1 Gly4 His0 LIe0 Lys3 Leu2 Met0 Pro4 Arg8 Ser2 Thr1 Val2 Tyr2, found Ala5.2 Asx4.8 CmCys0.6 Glx2.0 Phe1.0 Gly4.1 His0 LIe0 Lys2.9 Leu2.0 Met0 Pro3.7 Arg6.9 Ser1.8 Thr0.8 Val2.0 Tyr1.8; mass predicted 4786.4, found 4787.1.

For deprotection and purification of PPEBP2$^{SH}$, PAL resin (10 mg) containing protected PPEBP2$^{SH}$ was allowed to react for seven hours at room temperature in the deprotection cocktail and the solvent was removed. Diethylether (1 ml) and dithiothreitol (20 mg) were added, the supernatant was removed after centrifugation and the precipitate dried. The crude peptide was dissolved in 1 ml phosphate-buffered saline (pH 7.5) containing 5 mg fresh dithiothreitol and filtered. The peptide was purified by reversed phase HPLC (Vydac semipreparative 300 Å C18, 5 microns, 10.0×250 mm) using a linear 120 minute gradient of 100-50% Buffer A in Buffer B. The peptide eluted at 67.8 minutes using a flow rate of 4 ml/min and was characterized by electrospray ionization mass spectrometry: mass predicted 4654.2, found 4653.6.

For preparation of PPEBP2$^{SR}$, 0.070 mg of PPEBP2$^{SH}$ was dissolved in 0.50 ml of 2 mg/ml (15 mM) 2-bromoacetamide in 20 mM sodium phosphate buffer (pH 7.5). The reaction was allowed to proceed forty minutes at room temperature. The peptide was purified by reverse phase HPLC using a four minute linear gradient of 100-30% Buffer A in Buffer B (Rainin analytical 100 Å C18, 5 microns, 4.6×250 mm). PPEBP2$^{SH}$ eluted at 24.9 minutes using a flow rate of 1 ml/min, and was characterized by electrospray ionization mass spectrometry and amino acid analysis. AAA expected: Ala5 Asx6 CmCys1 Glx3 Phe1 Gly4 His0 LIe0 Lys3 Leu2 Met0 Pro4 Arg7 Ser2 Thr1 Val2 Tyr1, found Ala5.0 Asx5.8 CmCys0.9 Glx3.0 Phe1.0 Gly4.0 His0 LIe3.0 Lys3.0 Leu2.1 Met0 Pro4 Arg7 Ser2 Thr1 Val2 Tyr1; mass predicted 4711.3, found 4710.8.

For deprotection and purification of EBP1$^{SH}$, PAL resin (12 mg) containing protected EBP1$^{SH}$ was allowed to react for six hours at room temperature in the deprotection cocktail and treated as described for PPEBP1$^{SR}$. The crude peptide was dissolved in 1 ml phosphate-buffered saline (pH 7.5) with added dithiothreitol (5 mg) and filtered. The peptide was purified by reversed phase HPLC (Vydac semipreparative 300 Å C18, 5 microns, 10.0×250 mm) using a 72 minute linear gradient of 100-70% Buffer A in Buffer B. EBP1$^{SH}$ eluted at 49.6 minutes using a flow rate of 1 ml/min and was characterized by electrospray ionization mass spectrometry: mass predicted 3346.9, found 3346.2.

For preparation of EBP1$^{SR}$, 150 micrograms of EBP1$^{SH}$ was dissolved in 0.50 ml of 2 mg/ml (15 mM) 2-cromoacetamide in 20 mM sodium phosphate buffer (pH 7.5). The reaction was allowed to proceed thirty minutes at room temperature. The peptide was purified by reverse phase HPLC (Rainin analytical 100 Å C18, 5 microns, 4.6×250 mm) using a 40 minute linear gradient of 100-30% Buffer A in Buffer B. EBP1$^{SR}$ eluted at 17.0 minutes using a flow rate of 1 ml/min and was characterized by electrospray ionization mass spectrometry and amino acid analysis. AAA expected: Ala4 Asx3 CmCys1 Glx1 Phe1 Gly2 His0 LIe0 Lys3 Leu2 Met0 Pro0 Arg8 Ser1 Thr0 Val1 Tyr1, found Ala3.9 Asx3.0 CmCys0.9 Glx1.0 Phe1.0 Gly2.1 His0 LIe0 Lys2.8 Leu2.0 Met0 Pro1 Arg6.9 Ser0.9 Thr0 Val1.0 Tyr1.0; mass predicted 3404.0; found 3403.7.

For C/EBP$_{152}$, a stock solution of the purified C/EBP peptide was prepared by dissolution in phosphate-buffered saline with 10 mM dithiothreitol. The solution was heated to 95° C. and allowed to slowly cool to room temperature in order to assure reduction of the cysteine near the carboxy terminus of the peptide. The peptide was then used immediately for EMSA analysis. The peptide was characterized by amino acid analysis. AAA expected: Ala8 Asx18 Glx18 Phe5 Gly6 His0 LIe4 Lys14 Leu12 Met3 Pro6 Arg13 Ser15 Thr7 Val9 Tyr2, found Ala9.2 Asx16.9 Glx18.0 Phe4.5 Gly7.0 H0 LIe3.8 Lys14.2 Leu11.3 Met2.7 Pro6.0 Arg10.8 Ser13.0 Thr7.0 Val8.0 Tyr1.7.

Example 2

Binding of Miniature Proteins to DNA

Miniature protein-binding to DNA was measured using a electrophoretic mobility shift assay performed in a Model SE600 Dual-Controller Vertical Slab Unit (Hoefer) using 14×16 cm gel plates. Temperature was controlled using a constant temperature bath. Reactions were performed in a binding buffer composed of 137 mM NaCl, 2.7 mM KCl, 4.3 mM Na$_2$HPO$_4$, 1.4 mM NaH$_2$PO$_4$ (pH 7.4), 1 mM EDTA, 0.1% NP-40, 0.4 mg/ml BSA (non-acetylated) and 5% glycerol. For experiments involving the bZIP peptide C/EBP$_{152}$, the binding buffer was supplemented with 2 mM dithiothreitol. Serial peptide dilutions were performed as 1:1 dilutions with binding buffer. In general, 0.002 ml of gamma $^{32}$P-labeled, double-stranded DNA (CRE$_{24}$, hsCRE$_{24}$, C/EBP$_{24}$ or hsCEBP$_{24}$; final concentration ≦50 pM in binding buffer; final concentration ≦5 pM for peptides with K$_{app}$<500 pM) in binding buffer were added to 0.008 ml of a serial peptide dilution on ice. Peptide-DNA mixtures were incubated for thirty minutes on ice and then applied to a pre-equilibrated, native polyacrylamide gel (8% acrylamide: bisacrylamide) prepared in 10 mM Tris buffer (pH. 8.1).

Gels were allowed to run 0.75 to 1.5 hours at 500 V and were dried on a Model SE1160 Drygel Sr. gel dryer (Hoefer). The gels were analyzed using a Storm 840 Phosphorimager (Molecular Dynamics). Amounts of free and bound DNA were quantified and analyzed using the program Kaleida-Graph 3.0 (Synergy Software). Dissociation constants were determined by fitting the data to the Langmuir equation=c $[(1+(K_{app}/peptide_T^n))^{-1}]$ where n=1 for $^{SR}$ and $EBP^{SR}$ and n=2 for $C/EBP_{152}$. In these equations, theta=cpm in protein-DNA complex/(cpm in protein-DNA complex+cpm free DNA); peptide$_T$=the total peptide concentration and c is an adjustable parameter representing the maximum value of theta ($c \leq 1$; for many peptides c was defined as 1). Values reported represent the average of at least three independent trials±the standard error. Error bars on the plots represent the standard error for each data point.

For determination of binding stoichiometry, binding reactions were performed in the same buffer used for EMSA experiments. Each reaction contained 200 nM $hsCRE_{24}$ and between 25 nM to 1600 nM $PPEBP1^{SR}$. The $hsCEBP_{24}$ concentration was determined by measuring the absorbance of each single stranded oligonucleotide at 260 nm. One strand of each duplex was labeled with gamma-$^{32}$P. A small amount (0.010 ml) of labeled DNA was added to a 0.002 mM stock of the same strand. The ensure that the labeled strand annealed completely to its complement, an excess of cold complementary strand was added and the mixture was allowed to anneal by heating to 95° C. for two minutes and slowly cooling to room temperature. Labeled $hsCEBP_{24}$ was added to the $PPEBP1^{SR}$ solution and the reaction incubated at 4° C. for thirty minutes before being applied to a native 8% (80:1 acrylamide:bisacrylamide) prepared in 10 mM Tris buffer (pH=8.0 at 4° C.). The gels were suspended in a chamber containing 10 mM Tris buffer that was kept at 4° C. by immersion in a water circulating temperature bath. The gels were dried and 20 quantified with a Phosphorimager (Molecular Dynamics).

No significant DNA binding was detected with peptides $PPBR0^{SR}$ (SEQ ID NO: 8), $PPBR10^{SR}$ (SEQ ID NO: 9) and $PPBR11^{SR}$ (SEQ ID NO: 10) which lacked one or more of these DNA-contact residues. High-affinity DNA binding was observed with a peptide that contained these three residues: The equilibrium dissociation constant ($K_d$) of the $PPBR2^{SR}$ (SEQ ID NO: 11) binding to hsCRE was 5 nM under conditions of physiological ionic strength. DNA affinity was enhanced further by selective alanine substitutions that increased the overall alpha-helical propensity of the peptide, producing the $PPBR4^{SR}$-$hsCRE_{24}$ complex whose $K_d$ was 1.5 nM under identical conditions. Formation of the $PPBR4^{SR}$-$hsCRE_{24}$ complex was unaffected by high concentrations of poly (dIdC)-(dIdC) (Garner & Revzin, (1981) Nucl. Acids Res. 9, 3047-3048; Fried & Crothers, (1981) Nucl. Acids Res. 9, 6505-6506) or a scrambled CRE site (NON) indicating that the high stability of $PPBR4^{SR}$-$hsCRE_{24}$ was not due primarily to nonspecific ionic interactions. Circular dichroism experiments indicated that like bZIP peptides (Weiss et al., (1990) Nature 347, 575-578; O'Neil, (1990) Science 249, 774-778), no detectable changes in secondary structure occurred. $PPBR4^{SR}$(SEQ ID NO: 12) attained a fully alpha-helical conformation only in the presence of specific DNA (The CD spectrum of $PPBR4^{SR}$was unchanged between 0.001 and 0.020 mM, indicating that no detectable changes in secondary structure occurred in this range. Addition of hsCRE DNA significantly increased the alpha-helix content of $PPBR4^{SR}$ while smaller changes were observed upon addition of hsCEBP DNA.

Although others have described monopartite DNA recognition by basic segment peptides, the affinities reported have been only moderate (60 nM-0.003 mM), and the complexes are stable only in very low ionic strength buffers (Park et al., (1996) J. Am. Chem. Soc. 118, 4235-4239; Morii et al., (1996) J. Am. Chem. Soc. 118, 10011-10012). $PPBR4^{SR}$ represents the first example of high affinity, monopartite, major groove recognition at physiological ionic strength.

Example 3

Role of Hydrophobic Core in Miniature Protein-Binding to DNA

The contribution of hydrophobic core formation on $PPBR4^{SR}$-$hsCRE_{24}$ complex stability was examined utilizing UV circular dichroism experiments. Circular dichroism spectra were recorded in PBS on an Aviv-202 CD spectrometer and were background corrected but not smoothed. Wavelength scans were performed at 4° C. between 200 and 260 nm at 1 nm intervals with a recording time of five seconds at each interval. Thermal denaturation curves were measured at 222 nm between 4° C. and 98° C. with 2° C. steps and one minute equilibration at each temperature. Mean residue ellipticity and percent helicity were calculated from the value at 222 nm after background correction.

$G_{27}$ lacked the polyproline helix and turn, whereas $PPBR4$-$delta^{SR}$ contained D-tryptophan at position four and leucine at position thirty-one. Modeling studies suggested that these substitutions would disrupt core formation by kinking the polyproline or the alpha-helix. The stability of the $G_{27}$-$hsCRE_{24}$ and $PPBR4$-$delta^{SR}$-$hsCRE_{24}$ complexes were 3.1 and 3.2 kcal·mol$^{-1}$ lower, respectively, than that of $PPBR4^{SR}$-$hsCRE_{24}$ complex. These data indicate that hydrophobic core formation stabilized the $PPBR4^{SR}$-$hsCRE_{24}$ complex by as much as 3 kcal·mol$^{-1}$.

Example 4

DNA Sequence Specificity of Miniature Protein Binding

The sequence specificity of $PPBR4^{SR}$ was examined by comparing its affinity for $hsCRE_{24}$ (SEQ ID NO: 13) to that for $hsCEBP_{24}$ (SEQ ID NO: 4), a sequence containing the half-site recognized by C/EBP bZIP proteins (FIG. 2) (Agre et al., (1989) Science 246, 922-926) using the electrophoretic mobility shift assay described above. This half-site (ATTGC) differs from the CRE half-site (ATGAC) by two base pairs and provides an excellent measure of base pair specificity (Suckow et al., (1993) EMBO J. 12, 1193-1200; Johnson, (1993) Mol. Cell. Biol. 13, 6919-6930). $PPBR4^{SR}$ displayed remarkable specificity for $hsCRE_{24}$. The specificity ratio $K_{rel}(K_d(hsCRE)/K_d(hsCEPB))$ describing preferred recognition of $hsCRE_{24}$ by $PPBR4^{SR}$ was 2600 (delta,delta-G=−4.4 kcal·mol$^{-1}$). By contrast, $G_{56}$ which comprised the bZIP element of GCN4, displayed low specificity. Specificity ratios of 118 and 180 were observed for binding of $CRE_{24}$ (SEQ ID NO: 3) by $G_{56}$ in preference to $CEBP_{24}$ (SEQ ID NO: 4) and $hsCRE_{24}$ in preference to $hsCEBP_{24}$ (delta,delta-G=−2.6 and −2.9 kcal·mol$^{-1}$, respectively). The relative specificities of $G_{56}$ and $PPBR4^{SR}$ were most recognizable when one considered the concentration of each protein required to bind one-half of the two DNA. For $PPBR4^{SR}$, this difference corresponded to a ratio of 2600, whereas for $G_{56}$, it corresponded to a ratio of eleven. $PPBR4^{SR}$ more readily distinguished the two base pair difference between $hsCRE_{24}$ and $hsCEBP_{24}$ than $G_{56}$ distinguished $CRE_{24}$ from $hsCEBP_{24}$, two sequences that differed by six of ten base pairs. These comparisons emphasize that PPBR4$^{SR}$ was considerably more selective than was GCN4, the protein on which its design was based.

Example 5

Construction of Synthetic Genes Encoding a Miniature Protein

As described into detail below, the phage display vector pJC20 was derived from the monovalent phage display vector pCANTAB5E (Pharmacia). pJC20 was prepared by inserting a synthetic gene encoding aPP between the unique Sfi I and Not I restriction sites found in pCANTAB5E. The synthetic aPP gene contained codons for optimal protein expression in E. coli and four restriction sites (Xma I, Age I, Bgl II and Pst I) absent in pCANTAB5E. These restriction sites allow for the efficient construction of genes encoding a variety of discrete miniature proteins as well as for the introduction of genetic diversity. The vector pJC21 was prepared by inserting a synthetic gene encoding residues 18-42 of PPBR4 between the unique Bgl II and Not I sites in pJC20. The identities of pJC20 and pJC21 were confirmed by automated DNA sequencing A synthetic gene for aPP was constructed using codons chosen to optimize expression in E. coli and incorporated four unique restriction sites to facilitate cassette mutagenesis. The 142 base pair duplex insert was generated by use of mutually primed synthesis and the oligonucleotides APP.TS (CTA TGC GGC CCA GCC GGC CGG TCC GTC CCA GCC GAC CTA CCC GGG TGA CGA CGC ACC GGT TGA AGA TCT GAT CCG TTT CTA CAA CGA CCT GCA GCA GTA CCT GAA CGT TGT TAC CCG TCA CCG TTA CGC GGC CGC AGG TGC G) (SEQ ID NO: 39) and APP.BS (CTA TGC GGC CCA GCC GGC CGG TCC GTC CCA GCC GAC CTA CCC CGG GTG ACG ACG CAC CGG TTG AAG ATC TGA TCC GTT TCT ACA ACG) (SEQ ID NO: 40) which overlap at nineteen base pairs. The reaction mixture (20 ml) contained 8 pmol APP.TS, 8 pmol APP.BS, 1× ThermoPol buffer (New England Biolabs), 2 mg BSA, 1 mM dNTPs, 25 mCi [gamma-$^{32}$P] ATP, 5 MM MgSO$_4$ and 2 ml Vent(exo-) DNA polymerase and was incubated at 94° C. for thirty seconds, 60° C. for thirty seconds and 72° C. for one minute. The major reaction product was purified from a denaturing (8 M urea) 10% acrylamide (29:1 acrylamide:bis-acrylamide) gel and amplified by PCR in a 0.100 ml volume containing 1,500 pmol of the primers CTA TGC GGC CCA GCC GGC CGG (SEQ ID NO: 41) and CGC ACC TGC GGC CGC GTA ACG (SEQ ID NO: 42), 0.010 ml template, 0.25 mM dNTPs, 5 MM MgSO$_4$, 1× ThermoPol buffer (New England Biolabs) and 2 ml Vent(exo-) (New England Biolabs). The PCR reaction was subjected to thirty cycles of denaturation (94° C. for thirty seconds), annealing (60° C. for thirty seconds) and extension (72° C. for one minute). The insert was digested with Sfi I at 50° C. in NEB buffer two for four hours. This buffer was then supplemented with NaCl to a final concentration of 100 mM and with Tris-HCl to a final concentration of 50 mM before digestion with Not I for four hours at 37° C. The resulting insert was ligated into the vector pCANTAB-5E (Pharmacia) in a reaction containing 800 units T4 DNA ligase (New England Biolabs), 50 mM Tris-HCl (pH 7.8), 10 mM MgCl$_2$, 10 mM DTT, 25 mg/ml BSA, 1 mM ATP, 250 ng pCANTAB5E at 16° C. for one and a half hours. The ligation products were transformed by electroporation into TG1 E. coli and the resulting plasmid designated pJC20. A synthetic gene for PPBR4 was generated by replacing fifty-seven base pair at the 3' end of the aPP synthetic gene (in pJC20) with the sequence encoding the C-terminal twenty-five amino acids of PPBR4.

The oligonucleotides PPBR4$^{TS}$ (GAT CTG AAG CGC TTT CGT AAC ACC CTG GCT GCG CGC CGT TCC CGT GCA CGT AAA GCT GCA CGT GCT GCA GCT GGT GGT TGC GC) (SEQ ID NO: 43) and PPBR4$^{BS}$ (CGC ACC TGC GGC CGC GCA ACC ACC AGC TGC AGC ACG TGC AGC TTT ACG TGC ACG GGA ACG GCG CGC AGC CAG GGT GTT ACG AAA GCG CTT CAG ATC TTC AAC C) (SEQ ID NO: 44) were annealed and phosphorylated on the 5' end to form the PPBR4 insert. The PPBR4 insert was ligated into pJC20 that had been previously digested with Bgl II and Not I and dephosphorylated with enzyme. The ligation reaction mixture contained 800 units T4 DNA ligase in 50 mM Tris-HCl (pH 7.8), 10 mM MgCl$_2$, 10 mM DTT, 25 mg/ml BSA, 1 mM ATP, 90 ng digested pCANTAB-5E and 8 ng annealed insert. After reaction, the ligation mixture was transformed into electrocompetent TG1 E. coli. The plasmid was designated pJC21. The sequences of all final constructs were confirmed by automated sequencing.

Example 6

DNA-Binding Miniature Protein Phage Library Construction

A 10 ml volume of 2×YT containing 100 mg/ml ampicillin and 2% glucose was innoculated with a 500 ml overnight culture of TG-1 E. coli containing the plasmids pJC20 or pJC21 and shaken at 37° C. to an OD$_{600}$=0.8. 4×10$^{10}$ pfu of M13 KO7 helper phage were added and shaking continued for an additional one hour. Cells were pelleted for fifteen minutes at 5000×g and resuspended in an equal volume of 2×YT containing 100 mg/ml ampicillin and 50 mg/ml kanamycin and grown for ten hours with shaking. Cells were pelleted by centrifugation at 5000×g for twenty minutes and the phage supernatant filtered through a 0.45 micron filter before precipitation with PEG/NaCl (20% w/v PEG-8000, 2.5 M NaCl in ddH$_2$O) on ice for forty-five minutes. Phage were pelleted at 13000×g for thirty minutes at 4° C. and resuspended in binding buffer.

Example 7

Expression of Miniature Proteins by M13 Phage

As a first step towards displaying miniature proteins on the surface of phage, the inventors sought to verify that aPP was expressed from the synthetic gene, which is under the control of a lac promoter. To this end, TG-1 E. coli harboring pJC20 were induced with isopropylthiogalactoside (IPTG), lysed and the cell lysates probed with a rabbit anti-aPP antibody (Peninsula Laboratories #RGG-7194) as described below.

TG1 cells containing pJC20 were grown for one hour at 30° C. in 2×YT containing ampicillin at 100 mg/ml and 2% glucose. Cells were pelleted by centrifugation at 5000×g and resuspended in an equal volume of 2×YT containing 100 mg/ml ampicillin and 1 mM IPTG, grown for three hours at 30° C. and then lysed by boiling in SDS sample buffer. Aliquots were loaded onto a Pharmacia Phast HOMO 20 gel and electrphoresed at 95 V until the solvent front ran off the gel. Proteins in the gel were transferred to an Immobilon-P membrane at 65° C. for one hour. The membrane was blocked for thirty minutes with TBST (20 mM Tris-HCl (pH 8.0), 150 mM NaCl, 0.05% Tween-20) containing 0.5% BSA and then incubated with a 1:10000 dilution of rabbit anti-aPP (Peninsula Laboratories RGG-7194) provided at 4 mg/ml. The membrane was then washed three times (five minutes per wash) with TBST and then incubated with TBST containing a goat anti-rabbit alkaline phosphatase conjugate (Santa Cruz sc-2007) at a 1:1000 dilution. After three five minute washes with TBST and a single wash with TBS (TBST lacking Tween-20), the membrane was stained with VISTRA ECF (Pharmacia) and visualized at 405 nm on a STORM 850 Phosphoimager (Molecular Dynamics).

For Western blots on phage particles, 10 ml of phage were produced and precipitated with PEG/NaCl as described above. The phage were then resuspended in 1 ml ddH$_2$O, precipitated with 200 ml of PEG/NaCl, resuspended in 100 ml ddH$_2$O and heated to 95° C. in SDS sample buffer for ten minutes. The phage proteins were then applied to a 10% SDS gel (29:1 acrylamide:bisacrylamide) and subjected to electrophoresis at 20 mA in Tris-glycine electrophoresis buffer until the solvent front ran off the gel. The separated proteins were transferred to an Immobilon-P membrane (Millipore) at 20 V for four hours using a TE62 unit (Pharmacia) containing Towbin buffer (20% MeOH, 25 mM Tris-HCl (pH 8), 192 mM glycine, 0.1% SDS (w/v)) at 4° C. After blocking with 5% nonfat milk in TBST for sixteen hours and washing twice (five minutes per wash) with TBST, the membrane was probed for thirty minutes with anti-aPP in TBST supplemented with 2.5% nonfat milk. The membrane was washed three times (five minutes per wash) with TBST, then exposed to a goat anti-rabbit antibody-alkaline phosphatase conjugate (Santa Cruz sc-2007) at a 1:5000 dilution in TBST supplemented with 2.5% nonfat milk for fifteen minutes. After washing three times (five minutes per wash) with TBST and two times (five minutes per wash) with TBS the membrane was stained with VIS-TRA ECF (Pharmacia) and visualized at 405 nm on a STORM 850 phosphorimager (Molecular Dynamics).

These experiments demonstrate clear evidence for IPTG-inducible expression of aPP fused to the minor capsid protein III of M13 bacteriophage. To investigate whether this fusion protein was assembled into viable phage particles, purified phage were, phage proteins resolved using SDS-PAGE and probed with the rabbit anti-aPP antibody. The Western blot clearly shows that the fusion protein containing aPP and protein III is incorporated into fully assembled M13 phage particles. No signal was observed when phage produced from pJC21 bearing cells were probed with the rabbit anti-aPP antibody Example 8

Functional Selection of DNA-Binding Miniature Proteins on Phage

As a first step towards the optimization of PPBR4, the inventors confirmed that phage displaying PPBR4 could be selected over phage bearing aPP when sorted on the basis of specific DNA-binding. Phage displaying either PPBR4 or its progenitor aPP were panned against magnetic beads coated with a twenty-four base pair duplex oligonucleotide containing the five base pair sequence recognized by PPBR4, half site CRE (hsCRE, ATGAC). The DNA was attached to streptavidin coated beads through a 3' biotin TEG (triethyleneglycol) linker (Glen Research). Panning was performed essentially as previously described and as set forth below (Choo & Klug, (1994) Proc. Natl. Acad. Sci. USA 91, 11163-11167).

For panning experiments, 0.5 mg of streptavidin-coated M-280 magnetic beads (Dynal) were washed six times with 50 ml of 2×B+W buffer (10 mM Tris-HCl (pH 7.5), 1 mM EDTA, 2.0 M NaCl). Each wash step was performed for two minutes. The beads were blocked by incubation in 50 ml of 1×B+W containing 6% nonfat milk for fourteen hours. The beads were then washed five times with 50 ml of 1×B+W and resuspended in 50 ml of 1×B+W containing approximately 1 mM duplex hsCRE242 carrying a 3' biotin label on one strand for twelve minutes. This procedure loaded approximately 75 pmol DNA per mg bead. The beads were then washed five times with 50 ml of phage binding buffer (phosphate buffered saline supplemented with 0.4 mg/ml BSA, 0.1% NP-40 and 2.5 mg of poly-dIdC). 1010 phage in a volume of 0.4 ml were added to the beads at 4° C. and incubated with rotation on a Labquake shaker rotisserie for two hours. Beads were washed five times for five minutes at 4° C. with wash buffer (phage binding buffer lacking poly-dIdC). Bound phage were eluted by the addition of wash buffer containing 4 M NaCl and an increase in temperature to 25° C. for two hours. 200 ml of the elution and 200 ml of phage not subject to panning were used to infect 7 ml of log phase TG-1 E. coli. After one hour, serial dilutions of infected cells were plated on SOBAG (SOB media supplemented with ampicillin to 100 mg/ml and 2% glucose) and grown for twelve hours at 30° C. Values of percent retention were calculated where percent retention=(output titer/input titer)×100.

In the present experiments, wash conditions were optimized to maximize differential retention of phage displaying PPBR4 and phage displaying aPP. In phosphate buffered saline (PBS) supplemented with 0.1% NP-40, 0.4 mg/ml BSA and 2.5 µg/ml poly-dIdC, the percent retention of PPBR4 phage on hsCRE beads was ten times greater than that of aPP phage. This result indicates that miniature proteins generated by protein grafting can be functionally selected on M13 phage.

Example 9

Isolation of Highly Selective DNA-Binding Miniature Proteins

Figure 3:
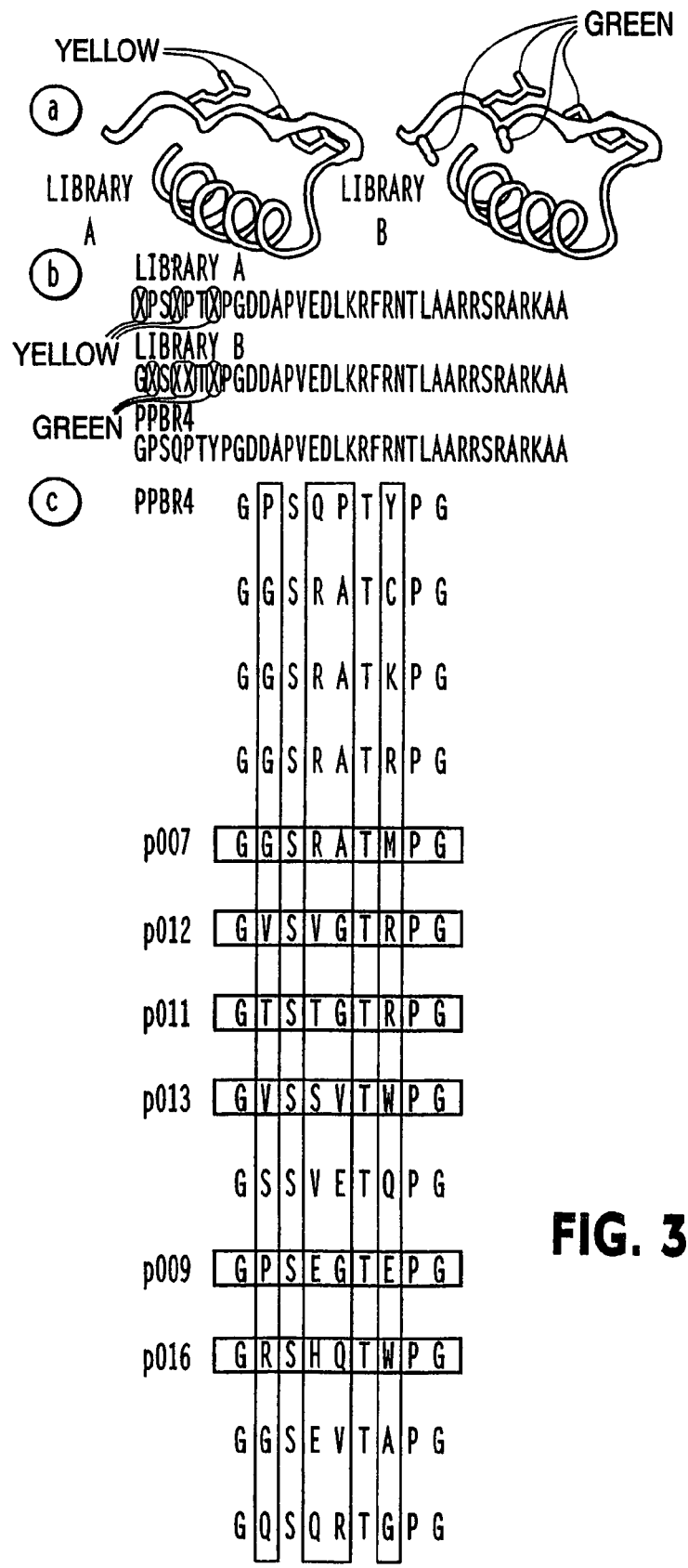
FIG. 3—(A) Residues of PPBR4 targeted for variation mapped onto the crystal structure of aPP. Side chains varied in library A are in yellow, those varied in library B are in green. (B) Sequences of PPBR4 and the two libraries. Residues varied are indicated by an X. Each position was randomized at the DNA level using the NNS codon scheme. (C) Sequences of the N-terminal amino acids deduced from the DNA sequences of the library B clones after three selection rounds. Peptides containing the boxed sequences followed by the remaining residues of PPBR4 were synthesized and their properties investigated in vitro. SEQ ID NOs: 15-22 are shown.

Two phage libraries were created essentially as described in the previous examples to identify appropriately folded PPBR4 analogs that would bind with higher affinity and specificity (FIG. 3). The members of libraries A and B differ from PPBR4 at three (library A) or four (library B) positions on the PPII helix. The proline residues retained at positions two and five of library A are highly conserved among PP-fold proteins. It was anticipated that retention of these two prolines would effectively constrain the conformational space available to library A members and that most would contain N-terminal PPII helices. Such conformational constraints are absent in library B, acknowledging that there may be many ways to stabilize DNA-bound alpha-helices.

Since the amino acids at positions two and five of library B are not restricted to proline, it was anticipated that this library would sample a larger fraction of available phi-psi space. Phage were sorted for three rounds on the basis of their ability to bind an oligonucleotide duplex containing the sequence ATGAC (hsCRE). To favor identification of sequences that bound hsCRE with high affinity at ambient temperature, two rounds of selection at 4° C. were followed by a single round at room temperature. By the final round, library A phage were retained at a level only comparable to PPBR4 phage and were not considered further. Library B phage were retained at a level comparable to PPBR4 phage after the first round, but at levels fifteen to sixteen times better than PPBR4 phage after the subsequent two rounds. Twelve library B clones were sequenced (FIG. 3c) after round three. Six sequences (p007, p009, p011, p012, p013, and p016) were synthesized and the DNA-binding properties of four analyzed in detail.

Quantitative electrophoretic mobility shift experiments were performed as described in the previous examples to assess the DNA affinities of p007, p011, p012, and p016. All peptides tested bound hsCRE as well or better than did PPBR4 or $G_{27}$ (the isolated basic region of GCN4). At 4° C., p011 and p012 bound hsCRE with affinities of 1.5±0.2 nM and 2.5±0.5 nM, whereas p016 bound hsCRE with an affinity of 300±60 pM. Of particular interest is p007, which bound hsCRE to form an exceptionally stable complex with a dissociation constant of 23±1.2 pM. This peptide bound specific DNA approximately 100-times better than did PPBR4 ($K_d$ 1.9±0.2 nM) and approximately 20,000 times better than did $G_{27}$ ($K_d$=410±53 nM). Moreover, at 25° C. p007 bound hsCRE with an affinity of 1.6±0.1 nM. Neither PPBR4 nor $G_{27}$ showed evidence of DNA binding at this temperature. P007 binds specific DNA considerably more tightly than two fingers from the Tramtrack zinc finger protein, which binds five base pairs of DNA with an affinity of 400 nM (Segal & Barbas, (2000) Curr. Op. Chem. Biol. 4, 34-35).

Example 10

Specificity of Highly Selective Miniature Protein DNA-Binding

The specificity of DNA binding was investigated by determining the affinity of p007 for several duplex oligonucleotides containing two base pair changes within the five base pair hsCRE sequence using quantitative electrophoretic mobility shift assays as described in the previous examples. p007 was extremely discriminating, exhibiting a specificity ratio R (defined as the ratio of the dissociation constants of specific and mutated complexes) between 200 and 800 (delta,delta-G=−3.3 to 4.0 kcal mol$^{-1}$). This high level of discrimination was observed across the entire five base pair hsCRE sequence, indicating that no single interaction dominated the free energy of the p007-hsCRE complex and that the binding energy is partitioned across the entire protein-DNA interface. By contrast, at 4° C. PPBR4 discriminates poorly (delta,delta-G=−1.7 kcal mol$^{-1}$) against sequences possessing mutations at the 5' terminus of hsCRE.

To investigate the possibility that DNA sequences other than these four might bind p007 tightly, the affinity of p007 for calf thymus DNA (CT DNA) which possesses a potential binding site in every register on either DNA strand was measured. The average specificity ratio for recognition of hsCRE in preference to any site in CT DNA was 4169. This ratio is considerably greater than the number of potential competitor sites ($4^5$=1024). Whereas the triple zinc finger construct Zif268 and variants thereof selected by phage display fail to uniquely specify one to two base pairs of their nine base pair binding sites (Li et al., (1992) Biochemistry 31, 1245-1253), p007 completely specifies all five base pairs of its target sequence. In fact, even if each possible five base pair competitor site were present at equal molarity to the target site, 80% of the p007 molecules would be bound to hsCRE, despite the effects of mass action.

Example 11

NMR Characterization of Miniature Protein Structure

For NMR Spectroscopy, p007 was dissolved in 90% H$_2$O/10% D$_2$O containing 4 mM KCl, 205 mM NaCl, 6.5 mM Na$_2$HPO$_4$, 2.1 mM KH$_2$PO$_4$ (pH 7.4). Peptide concentration was approximately 1.5 mM. Chemical shifts were referenced in ppm from internal 3-(trimethylsilyl)propionic-2,2,3,3-d4 acid, sodium salt. All spectra were recorded on a Varian 800 MHz Inova instrument at 2° C. with a sweep width of 9000 Hz. NOESY experiments were performed using a waterflip-watergate pulse sequence for water suppression with 4096t2×500t1 complex points. Mixing times of 50, 150 and 300 ms were acquired. DQF-COSY spectra (60 ms mixing time) were acquired with 2048t2×300t1 complex points. Data was processing was performed on a Silicon Graphics Workstation using Felix 98 (MSI). Prior to Fourier transform of the free induction decays, a gaussian window function was applied to NOESY spectra, while a Kaiser window function was applied to DQF-COSY spectra. The digital resolution of the NOESY spectra was 2.2 Hz/pt. DQF COSY data was zero filled to yield a 8192×8192 matrix with a digital resolution of 1.1 Hz. Spectra were assigned by standard methods.

Multidimensional NMR experiments allowed for characterization of the structure of p007 in greater detail. The backbone and side-chain connectivities in p007 were assigned on the basis of reasonably disperse NOESY spectra. The presence of amide-amide cross peaks between residues at positions i and i+3 and i and i+4 defined an alpha-helical conformation for residues 14-30. Eleven long range NOEs between residues 8 and 17, 8 and 20, 7 and 20, 5 and 20, 4 and 27, 2 and 29, 2 and 30 specify a folded structure that superimposes on residues 5-8 and 15-28 of aPP with a backbone rmsd of 1.6 Å. Thus, the main chain folds of p007 and aPP are remarkably similar, with residues 5, 7 and 8 proximal to residue 20 and residues 1 and 2 proximal to residue 30. As in previous studies of pancreatic fold polypeptides (Blundell et al., (1981) 78, 4175-4176), the PPII helix proposed for residues 1-8 of p007 is underdefined by the NMR data. However, in light of the similarity between the aPP and p007 folds, p007 must contain a structure similar to a PPII helix.

Example 12

Protein-Binding Miniature Protein Phage Library Construction

For construction of the aPPBAK library, mutagenesis was carried out using the NNS codon scheme, where N=any base and S=G/C. This scheme codes for all twenty amino acids and the amber stop codon TAG which is suppressed by insertion of glutamine in the E. coli SupE strains used. The oligonucleotides BAKLIB: GGT GAC GACGCA CCG GTT GAA GAT CTG ATC CGC TTT GTT NNS CGT CTG CTG NNS TAC ATC NNS GAC NNS ATC AAC CGT CGT GCG GCC GCA GGT GCG (SEQ ID NO: 45) and PBAK-LIB: CGC ACC TGC GGC GGCACG ACG (SEQ ID NO: 46) were synthesized and purified by denaturing gel electrophoresis. 400 pmol of each oligonucleotide were annealed in 1×Sequenase buffer (USB) in a total volume of 0.20 ml. The annealed oligonucleotides were converted to duplex DNA by primer extension upon addition of 2.5 mM dNTPs, 1 mg/ml BSA and 50 units Sequenase (USB) and incubation at 37° C. for thirty minutes. The duplex DNA was digested in 1×buffer 3 (New England Biolabs) by the addition of 0.015 ml Bgl II, 0.015 ml Not I, 2.5 MM DTT, 0.1 mg/ml BSA in a total volume of 0.430 ml. The reaction mixture was extracted twice with an equal volume of Tris buffered phenol (pH 8.0) and applied to a 15% acrylamide (29:1 acrylamide:bisacrylamide) gel in 1×TBE at 500 V. The doubly digested product was visualized by ethidium staining, excised and extracted in 1×TE. The insert was ethanol precipitated. 0.12 mg of the vector pJC20 was digested with 0.05 ml of Bgl II, Not I and Pst I in a total volume of 0.60 ml. The digested vector was purified by Chromaspin 1000 size exclusion chromatography (Clonetech) and phenol chloroform extraction followed by ethanol precipitation. Ligations were performed using the Ligation express kit (Clontech) with 830 ng of vector (pJC20) and 14 ng of insert. Transformation by electroporation in to TG-1 $E.$ $coli$ yielded $3×10^6$ transformants. The number of transformants is greater than the theoretical diversity of the library ($32^4=1.05×10^6$) and the library is statistically greater than 90% complete. Automated DNA sequencing of twenty clones showed the mutant genes were inserted correctly in all cases.

Example 13

Functional Selection of Protein-Binding Miniature Proteins on Phage

For biopanning of the aPPBAK library, a glutathione coated microtiter plate (Reacti-bind glutathione coated plate #15140, Pierce) was washed three times with 0.20 ml of PBS per wash. Human recombinant Bcl-2 (1-205) was obtained as a soluble GST-fusion from Santa Cruz Biotechnology. 9.0 pmol of Bcl-2 in 0.20 ml of PBS was added to each well and incubated at 4° C. for twelve hours with shaking. The wells were then blocked for three hours with 0.20 ml of TBST containing 5% nonfat dry milk. Before use, the well was washed three times with TBST for five minutes per wash.

Phage were produced, harvested and propagated as described in the previous examples, with the exception that, in rounds three through five, XL1-blue cells were used instead of TG-1 cells to propagate phage particles. This change eliminated problems encountered previously with deletions in later rounds of selection, which are attributed to the Rec A+ nature of TG-1 $E.$ $coli$. Phage particles were resuspended in 2 ml of TBST. 0.20 ml of phage ($1×10^{10}$ particles) were added to each well and incubated for three hours at 4° C. in the first two rounds of selection and at 25° C. in the final three rounds. The wells were then washed ten times with 0.20 ml of TBST, two minute washes in the first round and five minute washes in subsequent rounds. Washes were performed at the same temperature in the binding reaction. After five rounds of selection, sixteen clones were sequenced by automated DNA sequencing.

The phage library BAKLIB was subjected to five rounds of panning against immobilized GST-Bcl-2. The percent retention of the phage library increased 225-fold over the course of the selection from 0.01% in the first round to 2.25% in the fifth round. This increase in retention underestimates the improvement of library retention because the final round was carried out at 25° C. while the first round was performed at 4° C. After five rounds sixteen phagemid library clones were sequenced. The selected sequences (FIG. 4) show a high degree of convergence. Seven distinct sequences were isolated with four sequences represented multiple times. Interestingly, residue 28 in the library, which corresponds to $I_{81}$ of Bak, is mutated to F in eleven of sixteen round five clones, although it was fixed in the initial pool. This result indicates that within the context of the scaffold, $F_{28}$ is better at binding into the hydrophobic pocket of Bcl-2 than $I_{28}$. Eleven of sixteen sequences contain glycine at positions 75 and 82 as in Bak. Indeed, one sequence that was represented two of sixteen times contained residues identical to those of Bak at all four randomized positions, this sequence however, also contained the I-F mutation at position 28. Comparison of the selected sequences to other BH3-containing proteins reveals further similarities. For example, at position 26 of the library, R occurred in seven of the sixteen sequences and R or K is the preferred amino acid at this position (residue 79 in Bak) in most BH3 domains. Similarly, an E at position 31 of the library was selected in six of sixteen sequences, where E/D is the preferred amino acid at the corresponding position of most known BH3 domains.

The similarities of selected amino acids at these positions to those in Bak and other BH3 domains indicates that the sequences of BH3 domains arose from the requirement to bind Bcl-2 family proteins and not for other biological function. Further, it also indicates that the selected peptides bind Bcl-2 in the same hydrophobic pocket as does Bak. Interestingly, one sequence represented twice contained a threonine at position 31 of the library. This residue provides both the methyl group of a valine which could contribute to hydrophobic core formation and a hydroxyl group that could provide a hydrogen bond acceptor like the native D/E residue in BH3 domains. One sequence that appeared twice in the round five clones sequenced contained a single amino acid deletion with respect to the library design that places both the aPP folding residues and the Bcl-2 residues out of register.

Example 14

Synthesis of Protein-Binding Miniature Proteins

Peptides were synthesized on a 0.10 mM scale using Fmoc chemistry. Each peptide contained a free N-terminal amine and a C-terminal amide. Peptides were purified by reverse phase HPLC as described in the previous examples. Two sets of peptides were prepared, peptides 4099-4102 and the Bak peptide (SEQ ID NO: 73). Peptides for fluorescent labeling and subsequence $K_d$ determinations contained an additional carboxy-terminal YC sequence (the Y is derived from the native sequence of Bak), the cysteine of which was labeled with 5-iodoacetamidofluorescein (5IAF). Peptides at a final concentration of 200-400 mM were alkylated on the sulfur atom of C-terminal cysteines by incubation with ten equivalents of 5IAF (Molecular Probes) in 0.20 ml of a 50/50 mixture of DMF and PBS. The labeling reaction was performed in the dark for six hours at room temperature. Alkylation was essentially quantitative as judged by HPLC. Labeled peptides were purified by reverse phase C-18 HPLC. The identifies of the peptides were verified by MALDI-TOF mass spectrometry (Voyager, Perseptive Biosystems). The molecular weights were as expected: p4099 theoretical [MH+]=3907, observed [MH+]=3907; p4100 theoretical [MH+]=4020, observed [MH+]=4020; p4101 theoretical [MH+]=3921, observed [MH+]=3922; p4102 theoretical [MH+]=3901, observed [MH+]=3902; Bak 72-94 theoretical [MH+]=1724, observed [MH+]=1723; p4121-flu theoretical [MH+]=4562, observed [MH+]=4560; p4122 theoretical [MH+]=4675, observed [MH+]=4766; p4123 theoretical [MH+]=4576, observed [MH+]=4577; p4124 theoretical [MH+]=4556, observed [MH+]=4556;

Bak-flu theoretical [MH+]=2535, observed [MH+]=2535. Peptide concentrations were determined by amino acid analysis.

Example 15

Binding of Miniature Proteins to other Proteins

To measure the equilibrium dissociation constant of Bcl-2 binding to the selected peptides or the Bak BH3 peptide, Bcl-2 was serially diluted from 0.0036 mM in PBS with the fluorescently labeled peptide added at a constant concentration between 0.020-0.040 mM. After equilibration for forty minutes at 4° C., the fluorescein was excited at 492 nm using a PS-220B lamp power supply (Photon Technologies) and the fluorescence emission spectra between 505 and 560 nm recorded on an 814 photomultiplier detection system (Photon Technologies) with a 2 nm stepsize and a one second equilibration time, using 5 nm slit widths. The fluorescence emission maxima at 515 nm for three independent trials were averaged and the dissociation constants calculated as previously described (need ref). Similar experiments were used to determine the dissociation constants for the Bak peptide or selected peptides binding carbonic anhydrase II (Sigma) or calmodulin (Sigma). The calmodulin binding was measured in a buffer composed of 20 nM HEPES (pH. 7.2), 130 mM KCl, 1 mM $CaCl_2$ while carbonic anhydrase binding was measured in PBS.

The Bak peptide along with four sequences represented multiple times in the sixteen sequenced clones from round five were chemically synthesized. Bcl-2 binding affinity of the peptides was determined by measuring the change in fluorescence emission of a carboxy-terminal fluorescein label on the peptide as a function of Bcl-2 concentration. To validate this assay the $K_d$ for the Bak peptide binding to Bcl-2 was measured. This $K_d$ was 363 nM±56 nM, consistent with a $K_d$ of 340 nM previously reported for the Bak peptide Bcl-$X_L$ interaction (measured by fluorescence quenching of intrinsic tryptophan in Bcl-$X_L$) and a $K_d$ of about 200 nM reported for the Bak Bcl-2 interaction (measured by fluorescence polarization of a fluorescein labeled Bak peptide). The $K_d$ for the selected peptides were: p4099 $K_d$=352±33 nM, p4100 $K_d$=401±40 nM, p4101 $K_d$=811±20 nM, p4102 3700±1400 nM. The $K_d$ for all the peptides without deletions indicate that they bind significantly better than the mutant p4102 that contains a deletion in the alpha-helix. Within this series of peptides, p4099 (GAGT) binds about two-fold better than p4101 (GAGD), that differs in only a D to T mutation at position 31. p4100 (GRGE) binds with comparable affinity to p4099 indicating that these two peptides represent convergent and equal solutions to forming a protein-protein interface.

In order to compare the specificity of 4099 to the Bak peptide, their interaction with Calmodulin was investigated. Calmodulin is known to bind a range of alpha helices and Carbonic anhydrase II, which has a large hydrophobic cavity. p4099 bound Calmodulin with a $K_d$ of 0.025±0.004 mM, while the Bak peptide bound Calmodulin with a $K_d$ of 0.025±0.004 mM. p4099 bound Carbonic anhydrase II with a $K_d$ of 0.0086±0 mM, the Bak peptide bound Carbonic anhydrase with a $K_d$ of 0.022±0.0046 mM. p4099 discriminates well against these non-specific proteins indicating that the interaction between the peptide and Bcl-2 results from a stereospecific set of VanderWaals contacts.

Example 16

Structure of Protein-Binding Miniature Proteins

Circular dichroism spectra were recorded in PBS on an Aviv 202 CD Spectrometer and were background corrected but not smoothed. Wavelength scans were performed at 4° C. between 200 and 260 nm at 1 nm intervals with a recording time of five seconds at each interval. Bak (72-94), 4099, 4100, 4101, 4102 were used at concentrations of 0.028 mM, 0.0069 mM, 0.0119 mM, 0.014 mM and 0.016 mM respectively. Thermal denaturation curves were measured at 222 nm between 4-98° C. with 2° C. steps and one minute equilibration at each temperature. Peptides were used at the highest concentrations used for the wavelength scans described above. Mean residue elliptcity and percent helicity were calculated from the value at 222 nm after background correction.

The structure of peptides was investigated by far UV circular dichroism as described above. Wavelength scans reveal the previously reported random coil signature for the Bak peptide. In contrast the selected peptides 4099, 4100, 4101, 4102 show minima at 208 and 222 nm, characteristic of alpha-helical content. The mean ellipticity of peptide 4099 was shown to be concentration independent down to the lowest concentration measurable 0.0011 mM. The percentage helicity of p4099 is approximately 60%, consistent with an aPP-like tertiary fold in which residues 14-35 adopt a helical confirmation. This helicity is comparable to that seen for p007, a peptide evolved to bind DNA with high affinity and specificity as described in the previous examples. Thermal denaturation of the peptides was monitored by far UV circular dichroism at 222 nm. p4099 had a cooperative thermal melt with a $T_m$ of approximately 65° C., comparable to the $T_m$ reported for aPP.

Example 17

Miniature Proteins for Inhibiting hDM2-p53 Interactions hDM2 inhibits p53 by binding to the p53 activation domain (p53AD), inhibiting interaction of this domain with the transcriptional apparatus and targeting p53 for degradation. As few as fifteen amino acids of the p53AD support high-affinity interaction with hDM2. The alpha-helical segments of p53 and aPP are aligned in FIG. 5. This alignment positions the three critical hDM2 contact residues (Phe22, Leu29, and Trp26) on the exposed alpha-helical face of aPP without forsaking any aPP residues important for folding. Because many p53 residues within the p53AD-hDM2 structure display phi and psi angles outside the ideal alpha-helical range, diversity at five positions along the alpha-helix was introduced and selected for the highest affinity ligands using phage display. The library of M13 phage generated contained $6 \times 10^7$ transformants, a value that exceeds the theoretical diversity ($3.4 \times 10^7$). Phage were sorted for three rounds on the basis of their affinity for GST-hDM2 (residues 1-188) that had been immobilized on glutathione-coated 96-well plates. Weakly bound phage were removed by extensive washes and the bound phage eluted at low pH. Three selection rounds led to a 100-fold enrichment in affinity for GST-hDM2. Several peptides from round two and round three were synthesized and labeled at the C-termini with fluorescein for fluorescence polarization analysis.

To determine the affinity of each peptide for hDM2, varying concentrations of GST-hDM2 (50 nM to 0.002 mM) were incubated with a fixed concentration (25 nM) of labeled peptide at 4° C. for twenty minutes. The sample was irradiated at 492 nm and the fluorescence measured at 515 nm. A peptide containing p53AD (residues 15-33) was used as a positive control. Under the conditions of this assay, the p53AD-hDM2 complex was characterized by a $K_d$=261 nM when measured directly and 1.2 mM when measured by competition, verifying that the fluorescein moiety had no measurable effect on the stability of this interaction. When measured directly, each of the selected peptides displayed a high affinity for GST-hDM2, with dissociation constants in the nanomolar concentration range. One of the selected peptides, pZutshi (SEQ ID NO: 36), was significantly more potent than p53AD itself, binding GST-hDM2 with a $K_d$=99 nM±11 nM. Thus, pZutshi (p3559) which contains 31 amino acids, displays an activity similar to that of evolved protein antagonists in which the p53AD peptide (and variants thereof) is incorporated into the active site loop of the 109 residue thioredoxin.

In order to probe the specificity of the interaction between pZutshi and hDM2, we monitored the affinity of the miniature protein for a series of receptors and enzymes that bind helical or hydrophobic peptides or small molecules. Calmodulin, an EF hand protein notorious for its ability to bind many alpha-helical peptides and proteins, bound pZutshi modestly with an affinity in the millimolar concentration range ($K_d$~2.5 mM). Similar $K_d$ values were measured in analogous experiments performed with the bZIP region of Fos, which forms dimeric complexes with other bZIP proteins (42 µM), carbonic anhydrase, which binds $CO_2$ (0.298 mM) and protein kinase A (0.016 mM). The large difference between the stability of these complexes and that of the complex formed between pZutshi and GST-hDM2 (99 nM) suggests that the latter complex is specific and is stabilized by a highly stereo-specific set of van der Waals contacts.

A competition experiment was performed to establish whether pZutshi bound hDM2 in a manner that would inhibit the simultaneous binding of p53 and the concentration dependence of this inhibition. 400 nM GST-hDM2 and 10 nM p53AD-Flu was incubated with varying concentrations of pZutshi and monitored the fraction of p53AD-Flu bound at equilibrium. In the absence of pZutshi, approximately 60% of p53AD is bound under these solution conditions. Addition of pZutshi led to a concentration-dependent decrease ($K_i$=722 nM) in the fraction of p53AD bound to GST-hDM2. Similar $K_i$ values were determined at shorter and longer incubation times, indicating that equilibrium had been reached.

The secondary structure of pZutshi in the absence of hDM2 was investigated using circular dichroism spectroscopy. The CD spectrum of pZutshi was characterized by considerable negative ellipticity at 208 and 222 nm, as expected for a protein containing an a-helix. Temperature-dependent experiments showed that pZutshi undergoes a cooperative melting transition characterized by a $T_m$ of 47° C. The CD spectra at 0.00275 and 0.00675 mM were identical, suggesting that pZutshi undergoes no concentration-dependent conformational changes in this range and providing support that it exists as a well-folded monomer in solution. By contrast, the CD spectrum of p53AD showed little evidence of helical structure at 25° C.

Example 18

Miniature Proteins for Inhibiting Protein Kinase A

Three different potential miniature protein inhibitors of PKA (aPKI1, aPKI2, aPKI3) were designed by grafting residues from PKI, a known alpha helical peptide inhibitor of PKA, onto the exposed alpha helical surface of aPP. These potential miniature proteins differed in terms of how the residues important for binding PKA and folding aPP were aligned, and in terms of which type of residue was retained at positions of conflict. One miniature protein (aPKI2) bound and inhibited PKA and displayed a $K_d$=99 nM and an $IC_{50}$=8 nM, values similar to those measured for PKI itself ($K_d$=31.2 nM; $IC_{50}$=8 nM). In addition aPKI2 selectively inhibited PKA, unlike many small molecule inhibitors which mimic ATP. Work is in progress to characterize the inhibitory potential of aPKI2 tethered to such a small molecule kinase inhibitor, K252a, through an eight-carbon linker. K252a alone does not discriminate between PKA and PKC and displays an $IC_{50}$ value of 35 nM in experiments with PKA.

Example 19

Miniature Proteins for Activating Transcription through Interactions with the Co-Activator Protein CREB-Binding Protein (CBP)

In the first step of the grafting protocol, the region of CREB encompassing both the protein kinase A (PKA) recognition site and helix B (residues 130-146) was aligned with the alpha helix of aPP such that no conflicts occurred between residues required for phosphorylation by PKA, binding by CBP or folding of aPP. To facilitate identification of folded miniature proteins, a library of peptides for phage display that included (with one exception) all of these residues and all twenty amino acids at five positions along the aPP PPII helix was created. These positions are indicated by 'X' in the sequence GXS XXT XXG DDA PVR RLS FFY ILL DLY LDA P (SEQ ID NO: 69). The residue corresponding to Tyr134 of CREB was fixed as a Phe residue in the library; in the context of the CREB KID domain, the Tyr to Phe mutation does not affect affinity for KIX, yet lowers the $K_m$ for phosphorylation by PKA. It was reasoned that the Phe residue would play a similar role in the context of our grafted peptides and enhance their ability to be phosphorylated on the phage surface. Residues 2, 4, 5, 7 & 8 of the grafted peptides were randomized to all twenty amino acids plus the amber TAG stop codon in the library. The corresponding residues in the polyproline helix of aPP contribute to the hydrophobic core. Our library contained 5×10⁷ independent transformants, greater than the theoretical diversity of $32^5$=3.3×10⁷; statistically, the library was greater than 75% complete. The library phage were treated with protein kinase A and then sorted on the basis of binding to immobilized GST-KIX. Eight rounds of selection were performed, two rounds at 4° C. and six rounds at 25° C.

Twenty clones were sequenced from rounds six and seven, and thirty-eight clones were sequenced from round eight. One sequence (PPKID1): GAS DMT YWG DDA PVR RLS FFY ILL DLY LDA P (SEQ ID NO: 70) was found once in round six and once in round seven. Another sequence (PPKID2): GMS RVT PGG DDA PVR RLS FFY ILR DLY LDA P (SEQ ID NO: 72) was found once in round six, four times in round seven and nineteen times in round eight. Note this sequence contains a single amino acid mutation (Leu to Arg) as compared to the original library. A third sequence (PPKID3): GAS PHT SSG DDA PVR RLS FFD ILL DLY LDA P (SEQ ID NO: 73) was found twice in round seven and fourteen times in round eight. This sequence also contained a single amino acid mutation (Tyr to Asp) as compared to the original library, but a different mutation from that of PPKID2.

Synthetic peptides corresponding to each of these three sequences were prepared in both phosphorylated and unphosphorylated forms, labeled with acetamidofluorescein on a C-terminal Cys, and their affinities for the KIX domain of CBP measured by fluorescence polarization. Two peptides were synthesized for use as positive controls in these binding experiments. One, KID31, contained residues 119-148 of CREB, and was used to ensure that the assay provided an accurate measure of KIX-binding affinity. Phosphorylated KID31 bound GST-KIX with a $K_d$ of 0.0012 mM, a value similar to the reported value of between 550 and 750 nM. A second peptide KID20, containing residues 130-148 of CREB (i.e., the grafted residues), was used to measure KIX-binding affinity of the isolated helix B. Phosphorylated KID20 bound GST-KIX with a $K_d$ of 0.048 mM. In contrast, all three selected peptides bound GST-KIX with much higher affinity, both when phosphorylated, and albeit more weakly, also when unphosphorylated:phosphorylated PPKID1: $K_d$=31 nM, phosphorylated PPKID2: $K_d$=280 nM, unphosphorylated PPKID2: $K_d$=0.0076 mM, phosphorylated PPKID3: $K_d$=73 nM, unphosphorylated PPKID3: $K_d$=681 nM.

Example 20

Preparation of a Universal Miniature Protein Phage Display Library

Figure 6:
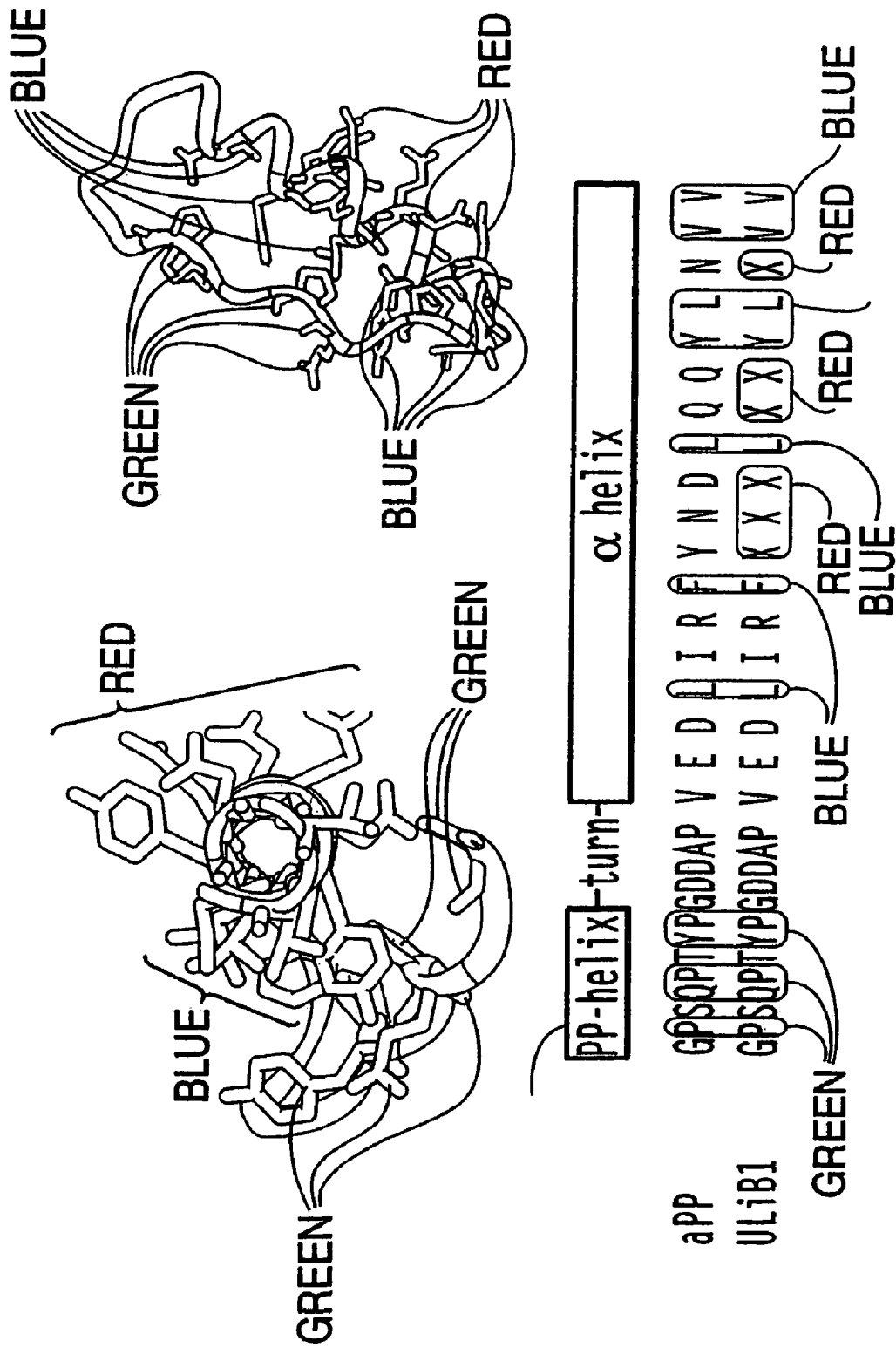
FIG. 6—Two views of the universal library that illustrate the relative orientation of the six residues chosen for variation (in beige) on the aPP solvent-exposed face (top). The image on the left sites along the alpha helix axis; the image on the right sites perpendicular to the alpha helix axis. Residues in blue contribute to forming the aPP hydrophobic core. Alignment of aPP and the universal library (bottom). Residues in blue stabilize the aPP hydrophobic core; residues in red are targeted for variation. SEQ ID NO: 38 is shown. The aPP sequence comprises residues 1-31 of SEQ ID NO: 6.

A combinatorial library designed to be used generally in the discovery and engineering of miniature proteins can also be constructed using the methods of the invention. This universal library is designed to display a combinatorial set of epitopes to enable the recognition of nucleic acids, proteins or small molecules by a miniature protein without prior knowledge of the natural epitope used for recognition. The universal library optimally is formed by varying (at least about) six residues on the solvent-exposed face of aPP which do not contribute to the formation of the hydrophobic aPP core (FIG. 6). These residues of aPP include Tyr21, Asn22, Asp22, Gln23 and Asn26. All members of this universal library will retain the remarkable stability and compact structure of avian pancreatic polypeptide while introducing a diverse, functional, solvent-exposed surface available for recognition. The number of independent transformants (2.5× $10^9$ clones) required to cover sequence space of a six-membered library is experimentally feasible.

Although the present invention has been described in detail with reference to examples above, it is understood that various modifications can be made without departing from the spirit of the invention. Accordingly, the invention is limited only by the following claims. All patents and publications referred to in this application are herein incorporated by reference in their entirety. The results of some of the experiments disclosed herein have been published (Zondlo & Schepartz, (1999) J. Am. Chem. Soc. 121, 6938-6939; Chin & Schepartz, (2001)123, 2929-2930).

What is claimed:

1. An avian pancreatic polypeptide of SEQ ID NO: 6, modified by substitution of amino acid residue positions 20-34 of SEQ ID NO: 6, wherein the substitution is an amino acid sequence selected from SEQ ID NOs: 23, 24, 25, 26, 27, 28, or 29.

2. The modified polypeptide of claim 1, wherein the modified avian pancreatic polypeptide binds to BCl-$X_L$ protein.

3. The modified polypeptide of claim 1, wherein the modified avian pancreatic polypeptide binds to Bcl2 protein.

4. The modified polypeptide of claim 1, wherein the substitution is SEQ ID NO: 25.

5. The avian pancreatic polypeptide of claim 1, wherein the substitution is SEQ ID NO: 23.

6. The avian pancreatic polypeptide of claim 1, wherein the substitution is SEQ ID NO: 24.

7. The avian pancreatic polypeptide of claim 1, wherein the substitution is SEQ ID NO: 26.

8. The avian pancreatic polypeptide of claim 1, wherein the substitution is SEQ ID NO: 27.

9. The avian pancreatic polypeptide of claim 1, wherein the substitution is SEQ ID NO: 28.

10. The avian pancreatic polypeptide of claim 1, wherein the substitution is SEQ ID NO: 29.

* * * * *